US012748118B2

(12) United States Patent
Liu et al.

(10) Patent No.: US 12,748,118 B2
(45) Date of Patent: Sep. 29, 2026

(54) FLUORESCENT ION INDICATORS AND THEIR APPLICATIONS

(71) Applicant: AAT Bioquest, Inc., Sunnyvale, CA (US)

(72) Inventors: Jixiang Liu, Pleasanton, CA (US); Zhenjun Diwu, Danville, CA (US); Deven Patel, Santa Clara, CA (US)

(73) Assignee: AAT Bioquest, Inc., Sunnyvale, CA (US)

(*) Notice: Subject to any disclaimer, the term of this patent is extended or adjusted under 35 U.S.C. 154(b) by 706 days.

(21) Appl. No.: 18/333,432

(22) Filed: Jun. 12, 2023

(65) Prior Publication Data

US 2024/0410907 A1 Dec. 12, 2024

(51) Int. Cl.

| | |
|---|---|
| ***C09K 11/00*** | (2006.01) |
| ***C07D 413/04*** | (2006.01) |
| ***C07D 413/10*** | (2006.01) |
| ***C07D 413/14*** | (2006.01) |
| ***C07D 491/22*** | (2006.01) |
| ***C07D 493/10*** | (2006.01) |
| ***C07D 495/10*** | (2006.01) |
| ***C07F 5/02*** | (2006.01) |
| ***C07F 7/08*** | (2006.01) |
| ***C07F 9/6568*** | (2006.01) |
| ***C09K 11/06*** | (2006.01) |
| ***G01N 1/30*** | (2006.01) |
| ***G01N 33/84*** | (2006.01) |

(52) U.S. Cl.

CPC ........... *G01N 33/84* (2013.01); *C07D 413/04* (2013.01); *C07D 413/10* (2013.01); *C07D 413/14* (2013.01); *C07D 491/22* (2013.01); *C07D 493/10* (2013.01); *C07D 495/10* (2013.01); *C07F 5/022* (2013.01); *C07F 5/025* (2013.01); *C07F 7/0816* (2013.01); *C07F 9/65681* (2013.01); *C07F 9/65685* (2013.01); *C09K 11/06* (2013.01); *G01N 1/30* (2013.01); *C09K 2211/1018* (2013.01); *G01N 2001/302* (2013.01)

(58) Field of Classification Search

CPC ...................................................... G01N 33/84
USPC ........................................................... 436/79
See application file for complete search history.

(56) References Cited

U.S. PATENT DOCUMENTS

| | | | |
|---|---|---|---|
| 4,603,209 | A | 7/1986 | Tsien et al. |
| 4,820,647 | A | 4/1989 | Gibbons |
| 4,849,362 | A | 7/1989 | DeMarinis et al. |

(Continued)

FOREIGN PATENT DOCUMENTS

| | | | |
|---|---|---|---|
| CN | 108774241 | A | 11/2018 |
| WO | WO 2005/016872 | A1 | 2/2005 |
| WO | WO 2007/113854 | A1 | 10/2007 |
| WO | 2011/047391 | A1 | 4/2011 |

OTHER PUBLICATIONS

Feng et al. "A highly selective fluorescent probe for the determination of Se(IV) in multivitamin tablets," Sensors and Actuators B: Chemical vol. 193, 2014, pp. 592-598.

(Continued)

*Primary Examiner* — Lyle Alexander
*Assistant Examiner* — Emily R. Berkeley
(74) *Attorney, Agent, or Firm* — Fenwick & West LLP

(57) ABSTRACT

Fluorescent dyes useful for preparing fluorescent metal ion indicators, the fluorescent indicators themselves, and the use of the fluorescent indicators for the detection, discrimination and quantification of metal cations are provided.

32 Claims, 10 Drawing Sheets

(56) References Cited

U.S. PATENT DOCUMENTS

| | | | |
|---|---|---|---|
| 5,049,673 | A | 9/1991 | Tsien et al. |
| 5,134,232 | A | 7/1992 | Tsien et al. |
| 5,136,033 | A | 8/1992 | Masilamani et al. |
| 5,405,975 | A | 4/1995 | Kuhn et al. |
| 5,453,517 | A | 9/1995 | Kuhn et al. |
| 5,459,276 | A | 10/1995 | Kuhn et al. |
| 5,501,980 | A | 3/1996 | Katerinopoulos et al. |
| 5,516,911 | A | 5/1996 | London et al. |
| 5,773,227 | A | 6/1998 | Kuhn et al. |
| 7,129,346 | B2 | 10/2006 | Gee et al. |
| 7,989,617 | B2 | 8/2011 | Gee et al. |
| 8,389,505 | B2 | 3/2013 | Kralj et al. |
| 8,927,224 | B2 | 1/2015 | Diwu et al. |
| 9,346,778 | B2 | 5/2016 | Diwu et al. |
| 2014/0363839 | A1 | 12/2014 | Gee et al. |
| 2022/0200042 | A1 | 6/2022 | Ignacio de Leon et al. |

OTHER PUBLICATIONS

Lavis, "Live and Let Dye," Biochemistry 2021, 60, 46, pp. 3539-3546.

Le Guern et al., "Fluorescein Derivatives as Fluorescent Probes for pH Monitoring along Recent Biological Applications," Int J Mol Sci. Dec. 3, 2020; 21(23):9217, 23 Pages.

Liu et al. "Synthesis and Analytical Application of a Novel Fluorescent Hg2+ Probe 3', 6'-Bis(Diethylamino)-2-((2,4-Dimethoxybenzylidene)Amino)Spiro[Isoindoline-1,9'-Xanthene]-3-Thione," J Fluoresc, 2013, 23, pp. 989-996.

Ni et al. "A novel fluorescent probe based on rhodamine B derivative for highly selective and sensitive detection of mercury(II) ion in aqueous solution," Sensors and Actuators B: Chemical vol. 186, 2013, pp. 278-285.

Patel et al., "A highly selective fluorescent probe for the intracellular measurement of magnesium ion," Analytical Biochemistry vol. 609, 2020, 113910, 4 Pages.

Chen, C-A., et al., "Design and Synthesis of a Fluorescent Reporter of Protein Kinase Activity," *Journal of the American Chemical Society,* Mar. 2002, vol. 124, Issue 15, pp. 3840-3841, https://doi.org/10.1021/ja017530v.

Eidelman, O., et al., "Continuous monitoring of transport by fluorescence on cells and vesicles." Biochimica et Biophysica Acta (BBA)—Reviews on Biomembranes, vol. 988, Issue 3, Dec. 6, 1989, pp. 319-334.

Urano, Y., et al., "Evolution of Fluorescein as a Platform for Finely Tunable Fluorescence Probes," Journal of the American Chemical Society, Mar. 2005, vol. 127, Issue 13, pp. 4888-4894, https://doi.org/10.1021/ja043919h.

FLUORESCENT ION INDICATORS AND THEIR APPLICATIONS

BACKGROUND

Metal ions play important roles in many biological systems. Cells utilize metal ions for a wide variety of functions, such as regulating enzyme activities, protein structures, cellular signaling, as catalysts, as templates for polymer formation and as regulatory elements for gene transcription. Metal ions can also have a deleterious effect when present in excess of bodily requirements or capacity to excrete. A large number of natural and synthetic materials are known to selectively or non-selectively bind to or chelate metal ions. Ion chelators are commonly used in solution for in vivo control of ionic concentrations and detoxification of excess metals, and as in vitro buffers. Ion chelators can be used as optical indicators of ions when bound to a fluorophore, and may be useful in the analysis of cellular microenvironments or dynamic properties of proteins, membranes and nucleic acids. For example, $Na^+$ and $K^+$ ions play an important role in many biological events, and so the determination of intracellular $Na^+$ and $K^+$ is an important biological application (see U.S. Pat. No. 5,134,232). There are a steadily increasing number of publications that reported the biological activities of $Li^+$ ion (See B. Shahzad et al., Environmental Science and Pollution Research 2017, 24(1), DOI: 10.1007/s11356-016-7898-0). In addition, lithium ion plays a crucial role in the new energy industry (see U.S. Pat. Appl. No. 2022/0200042).

Fluorescent indicators utilizing a crown ether chelator have been predominantly used for intracellular metal ion detections (see U.S. Pat. Nos. 4,820,647; 5,136,033; 5,134,232; 7,129,346; 7,989,617; 8,389,505; U.S. Pat. Appl. No. 2014/0363839; WO 2005/016872 and WO 2007/113854). SBFI and PBFI are the most common fluorescent indicators used for determining $Na^+$ and $K^+$ in biological assays (see U.S. Pat. No. 5,134,232). However, these existing $Na^+$ and $K^+$ indicators typically have low fluorescence quantum yields, short excitation and emission wavelengths, resulting in low detection sensitivity and high assay background. Furthermore, their corresponding acetoxymethyl esters may not readily penetrate the membranes of live cells (thus requiring higher temperatures to achieve optimal dye loading), and once inside the cells, they exhibit a slow conversion to the corresponding crown ether free acid.

In view of the existing drawbacks for currently used fluorescent $Na^+$ and $K^+$ indicators, what is needed are improved compositions and methods that offer sensitive detection of small variations in $Na^+$ and $K^+$ concentrations, with a rapid response and a strong fluorescence signal. Also needed are fluorescent indicators that can be readily loaded into live cells. In addition, compositions and methods that are less susceptible to the effects of external changes (such as pH and temperature) are preferred for high throughput screening and high content analysis. So far there are no sensitive fluorescent indicators reported that can be used to detect $Li^+$ ion in aqueous solutions.

SUMMARY

The present application is directed to a family of fluorescent dyes that are useful for preparing fluorescent $Li^+$, $Na^+$ and $K^+$ indicators. The indicators include a fluorophore condensed with an ionophore and are useful for the detection, discrimination and quantification of metal cations in solutions, tissues and other materials. Another class of the indicators are xanthene fluorophore or xanthene lactone fluorophore condensed with an ionophore. They are useful for detecting metal cations in live cells and other biological samples that contain esterases and other hydrolases. Another class of the indicators are pyrrole fluorophores condensed with an ionophore. They are useful for detecting metal cations in live cells and other biological samples that contain esterases and other hydrolases. The fluorescent indicators of this invention demonstrate unexpected, better cellular and spectral properties compared to the existing fluorescent ion indicators.

BRIEF DESCRIPTION OF THE DRAWINGS

As shown in FIG. 1, Compound 8 exhibits a much longer absorption wavelength than SBFI. A longer absorption wavelength minimizes the background caused by naturally occurring biological substances.

As shown in FIG. 2, Compound 12 exhibits a much longer absorption wavelength than PBFI. A longer absorption wavelength minimizes the background caused by naturally occurring biological substances.

As shown in FIG. 3, Compound 8 exhibits a much stronger and sharper fluorescence emission peak (top curve) than SBFI (bottom curve). The strong and sharp fluorescence emission peak is a critical characteristic required for multicolor analysis.

As shown in FIG. 4, Compound 12 exhibits a much stronger and sharper (top curve) than PBFI (bottom curve). The strong and sharp is a critical characteristic required for multicolor analysis.

As shown in FIG. 5, Compound 8 exhibits a much stronger sodium ion response than SBFI under the same conditions. SBFI=Black column; Compound 8=Grey column.

As shown in FIG. 6, Compound 12 exhibits a much stronger potassium ion response than PBFI under the same conditions. PBFI=Black column; Compound 12=Grey column.

μM Compound 8. The fluorescence intensities measured and recorded for all the solutions under the same conditions.

Figure 1:
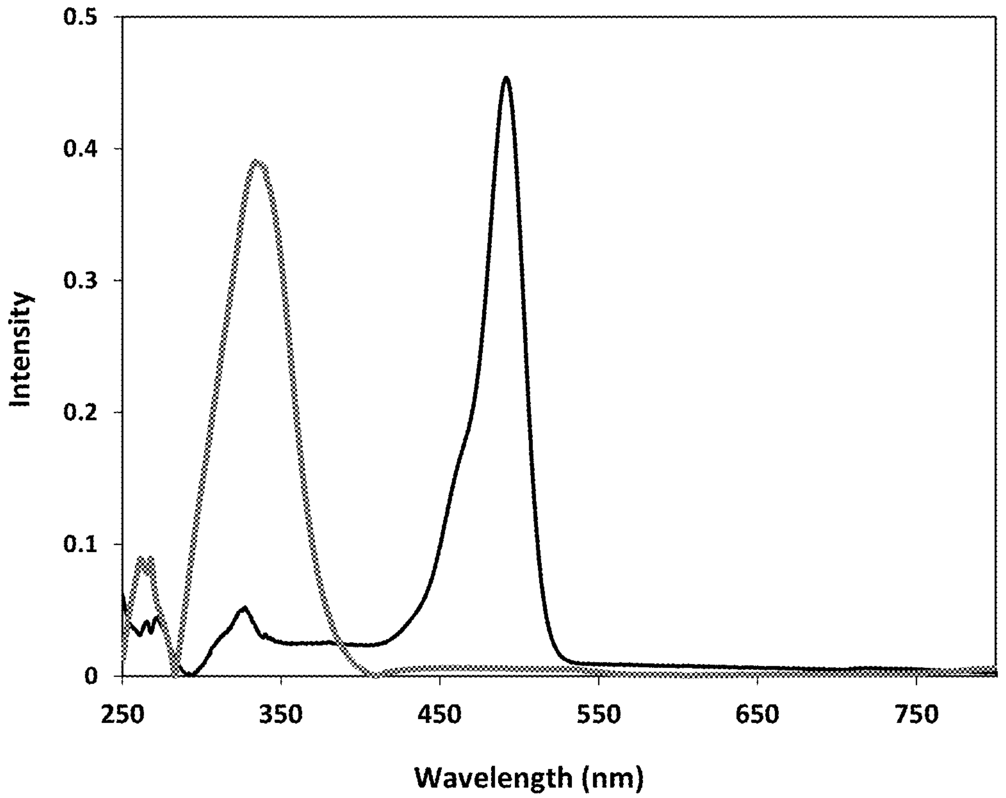
FIG. 1. The absorption spectral comparison of SBFI and Compound 8. SBFI (10 μM) and Compound 8 (10 μM) are dissolved in TRIS buffer (pH 7.0). The absorption spectra are recorded in the presence of 100 mM NaCl.
Figure 2:
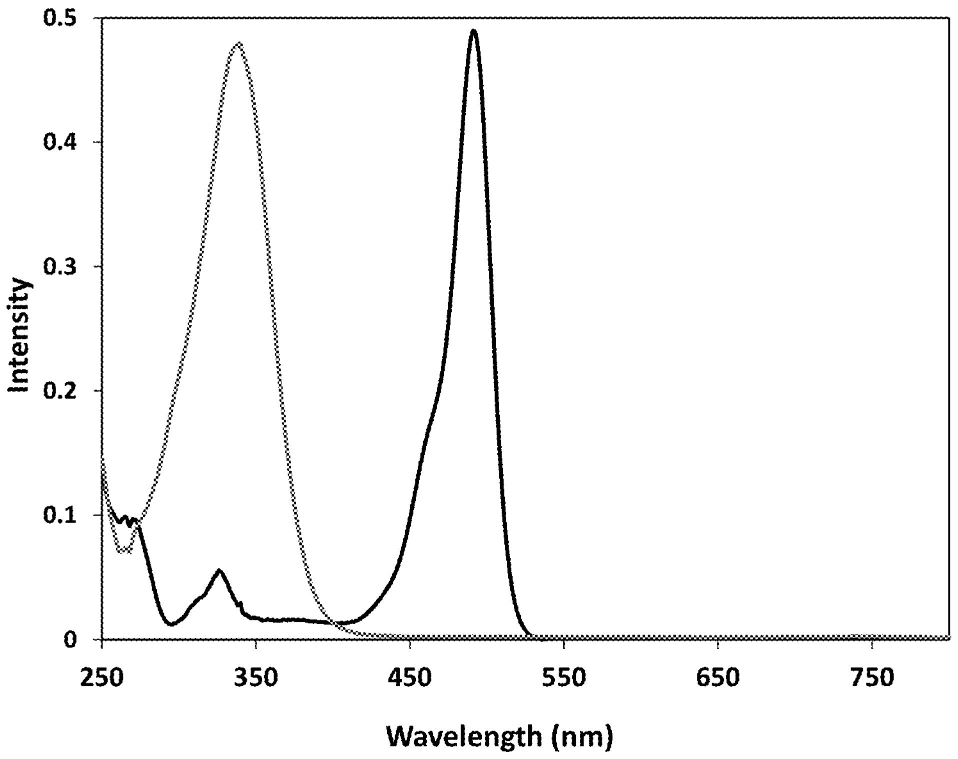
FIG. 2. The absorption spectral comparison of PBFI and Compound 12. PBFI (10 μM) and Compound 12 (10 μM) are dissolved in TRIS buffer (pH 7.0). The absorption spectra are recorded in the presence of 100 mM KCl.
Figure 3:
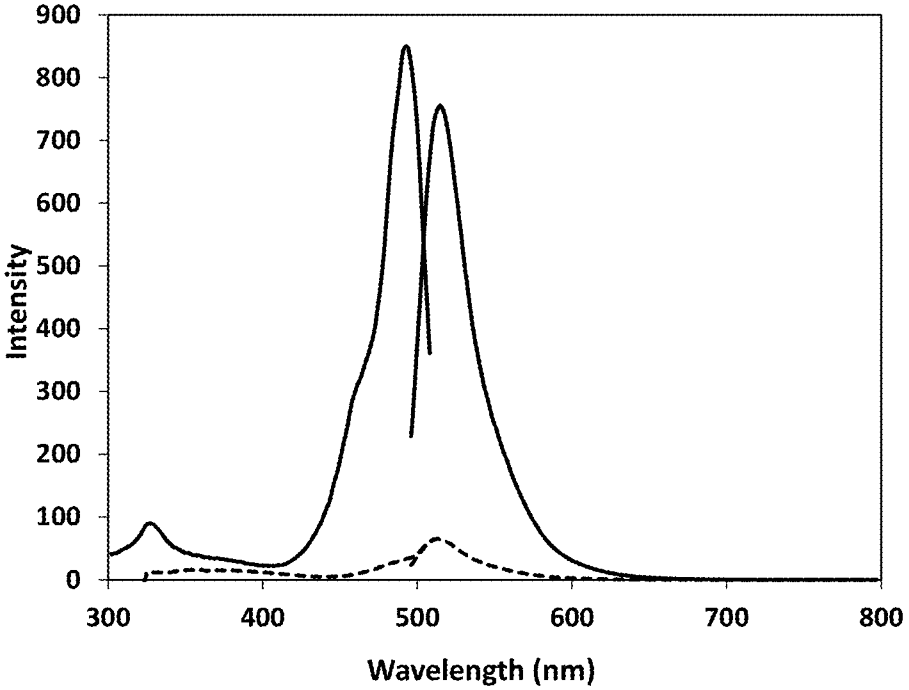
FIG. 3. The spectral comparison of SBFI and Compound 8. SBFI (2.5 μM) and Compound 8 (2.5 μM) are dissolved in TRIS buffer (pH 7.0). The excitation and fluorescence spectra are recorded in the presence of 100 mM NaCl.
Figure 4:
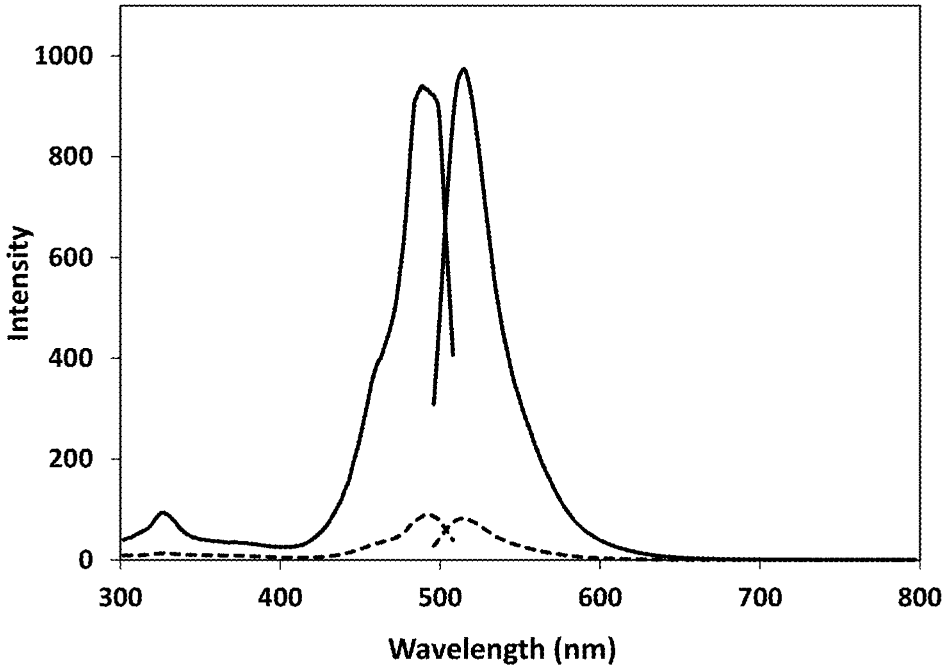
FIG. 4. The spectral comparison of PBFI and Compound 12. PBFI (2.5 μM) and Compound 12 (2.5 μM) are dissolved in TRIS buffer (pH 7.0). The excitation and fluorescence spectra are recorded in the presence of 100 mM KCl.
Figure 5:
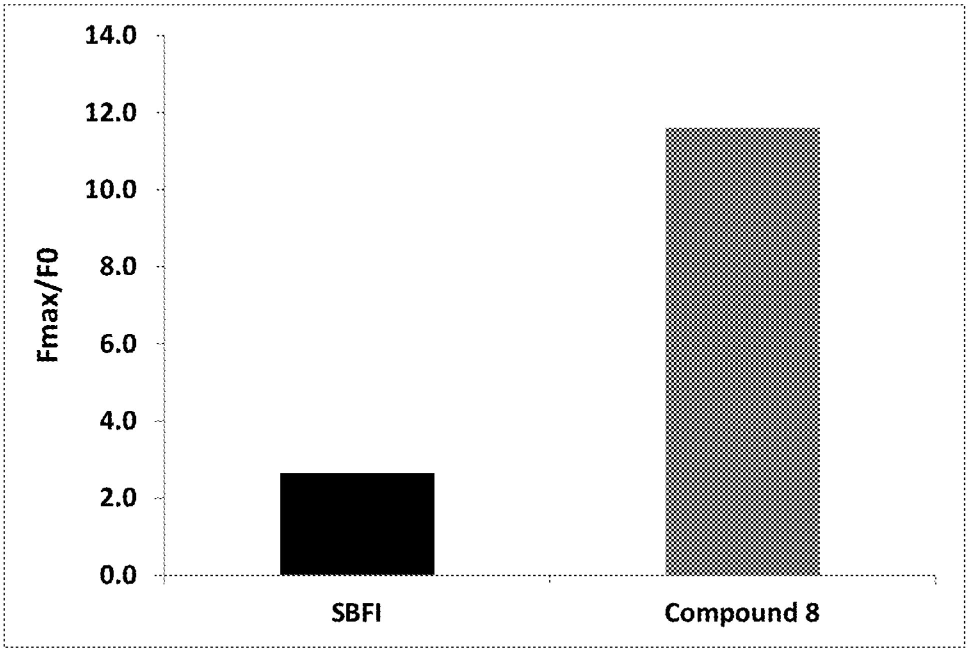
FIG. 5. Comparisons of Compound 8 and SBFI to sodium ion responses. SBFI (2.5 μM) and Compound 8 (2.5 μM) are added in Tris-HCl buffer (pH-7) with 60 mM NaCl ($F_{max}$) or without NaCl ($F_0$) and their fluorescence intensities are recorded.
Figure 6:
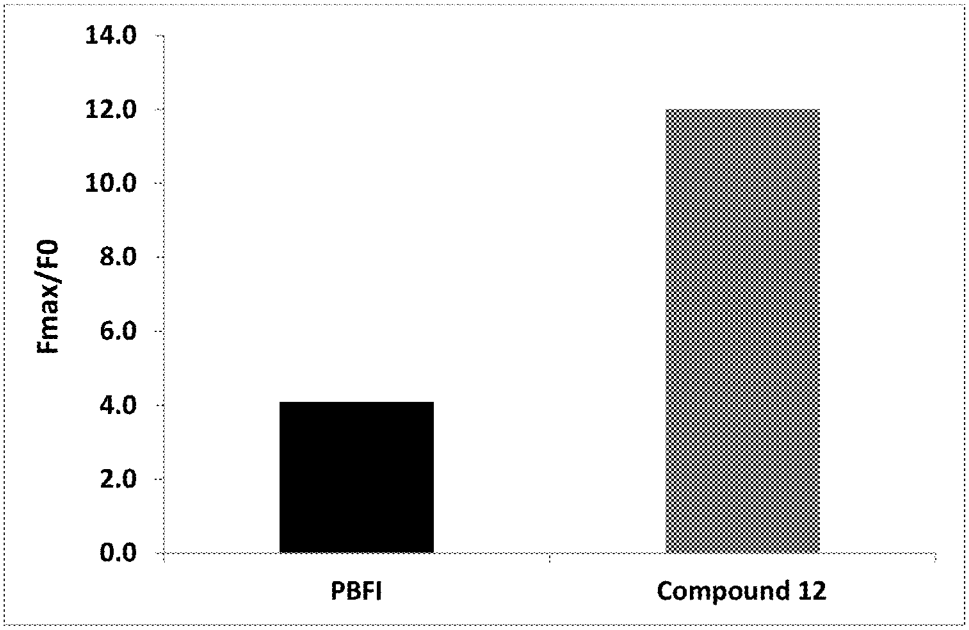
FIG. 6. Comparisons of Compound 12 and PBFI to potassium ion responses. PBFI (2.5 μM) and Compound 12 (2.5 μM) are added in Tris-HCl buffer (pH 7.0) with 60 mM KCl ($F_{max}$) or without KCl ($F_0$) and their fluorescence intensities are recorded.
Figure 7:
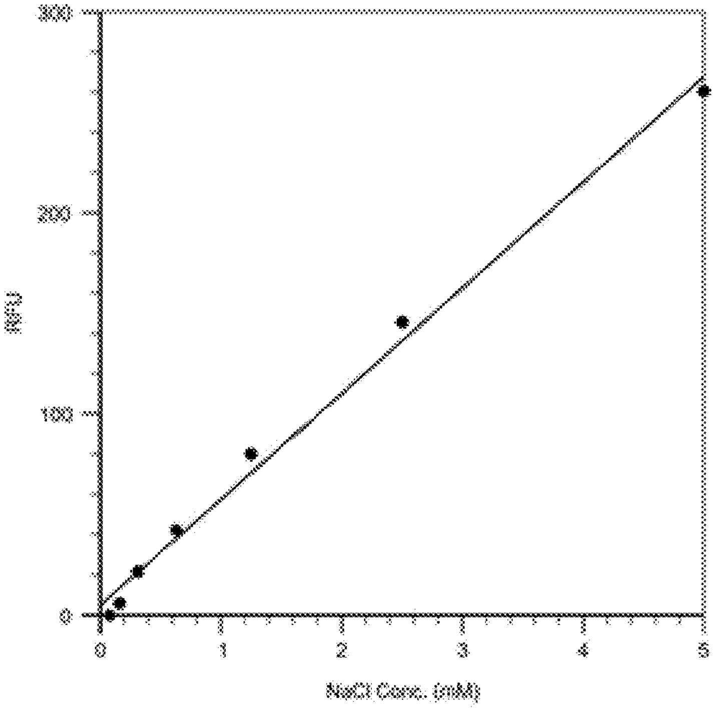
FIG. 7. Sodium ion responses of Compound 8. Compound 8 is dissolved in Tris-HCl (pH 7.0) to make a dye stock solution. The equal amount of Compound 8 is added to a variety of NaCl solutions with all the solutions having 2.5
Figure 8:
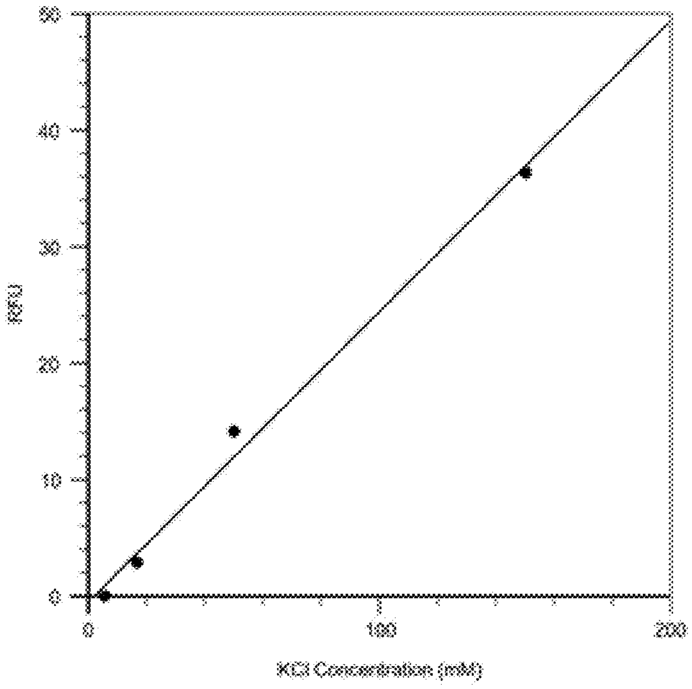

FIG. 8. Potassium ion responses of Compound 12. Compound 12 is dissolved in Tris-HCl (pH 7.0) to make a dye stock solution. The equal amount of Compound 12 is added to a variety of KCl solutions with all the solutions having 2.5 μM Compound 12. The fluorescence intensities measured and recorded for all the solutions under the same conditions.

Figure 9:
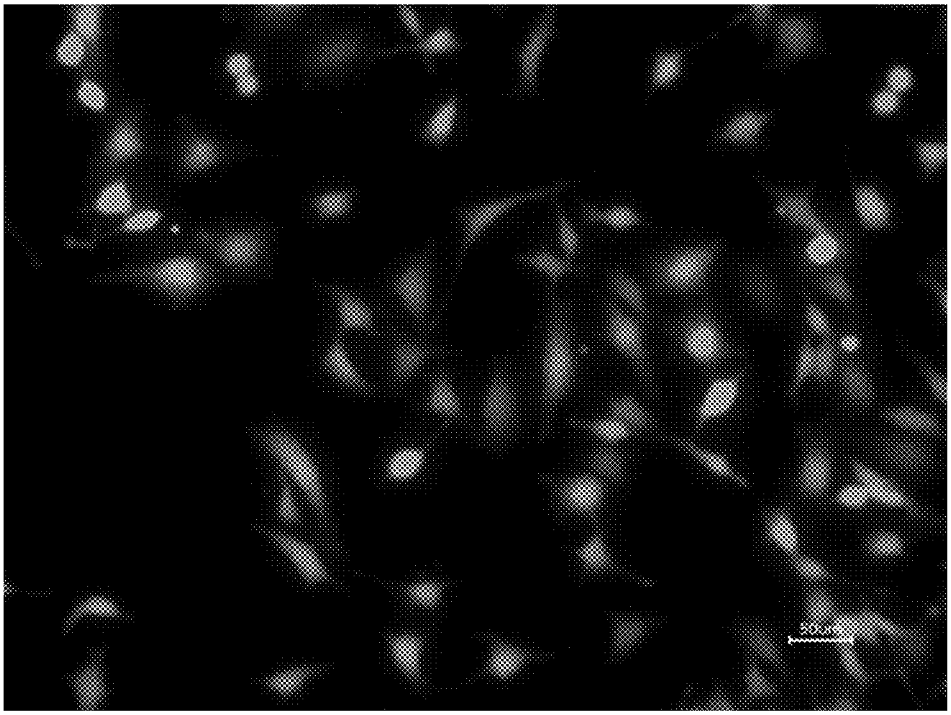

FIG. 9. Intracellular imaging of live cells with Compound 17. HeLa cells are plated overnight in growth medium (DMEM). On the next day, growth medium is removed, and cells are washed with PBS. Compound 17 is dissolved in HHBS buffer containing 0.02% PF-127 to make a 10 μM dye working solution. 200 μL of the dye working solution is added. Cells are incubated at 37° C. and incubated for 30 minutes. The dye working solution is removed and HHBS buffer is added. The fluorescence images are acquired with Keyence BZ-X710 fluorescence microscope with FITC filter set.

Figure 10:
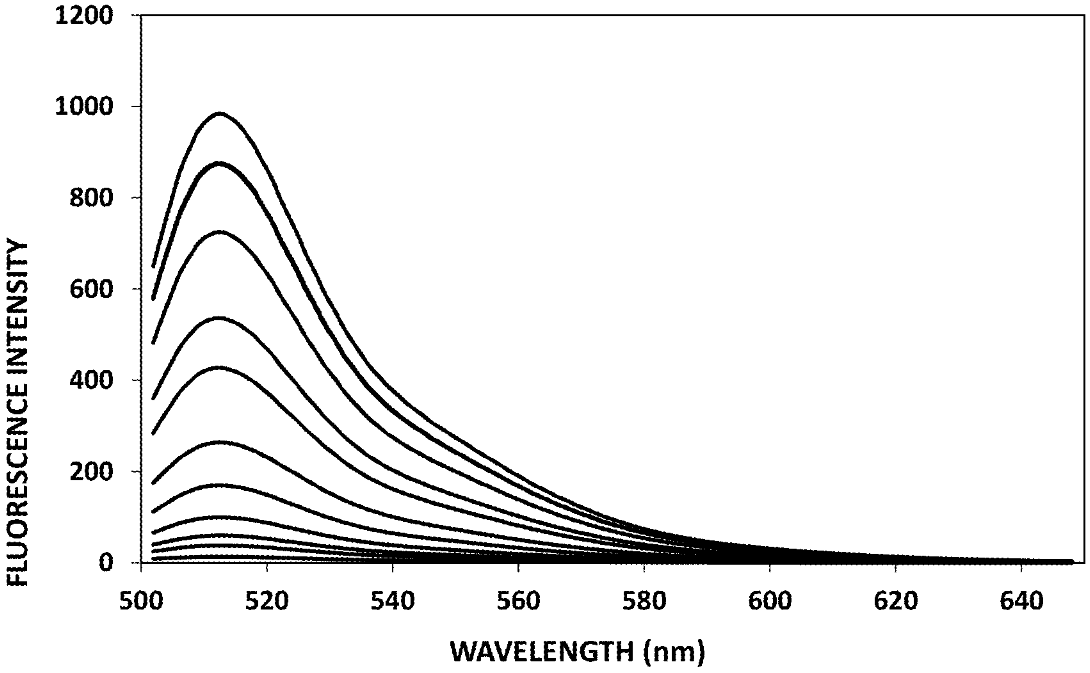

FIG. 10. Lithium ion responses of Compound 15. Compound 15 is dissolved in Tris-HCl (pH 7.0) to make a dye stock solution. The equal amount of Compound 15 is added to a variety of LiCl solutions with all the solutions having 2.5 μM Compound 15 and LiCl concentrations varied from 0, 0.62, 1.85, 5.56, 16.67, 50, 150, 450 mM (from bottom to top). The fluorescence intensities measured and recorded for all the solutions under the same conditions.

DEFINITIONS

The following definitions are set forth to illustrate and define the meaning and scope of the various terms used to describe the invention herein.

The term "organic substituent", as used herein, refers to a carbon-containing organic radical that incorporates straight, branched chain or cyclic radicals having up to 50 carbons, unless the chain length or ring size is limited thereto. The organic substituent may include one or more elements of unsaturation, such as carbon-carbon double or triple bonds. Organic substituents may include alkyl, alkylene, alkenyl, alkenylene and alkynyl moieties, among others.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species.

For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species and therefore each subset is considered separately disclosed. For example, the term $C_1$-$C_4$alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "alkyl" also encompasses cycloalkyl or carbocyclic groups. For example, when a term is used that includes "alk" then "cycloalkyl" or "carbocyclic" can be considered part of the definition, unless unambiguously excluded by the context. For example and without limitation, the terms alkyl, alkoxy, haloalkyl, etc. can all be considered to include the cyclic forms of alkyl, unless unambiguously excluded by context.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one triple bond.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$ alkylene, $C_1$-$C_3$ alkylene, $C_1$-$C_4$ alkylene, $C_1$-$C_6$ alkylene, or $C_1$-$C_6$ alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

The term "alkoxy" as used herein, by itself or as part of another group, refers to any of the above radicals (e.g., alkyl) linked via an oxygen atom. Typical examples include methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy, among others. Alkoxy also may include PEG groups ($—OCH_2CH_2O—$) or alkyl moieties that contain more than one oxygen atom.

The term "amino" refers to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

"Chain" indicates a linear chain to which all other chains, long or short or both, may be regarded as being pendant. Where two or more chains could equally be considered to be the main chain, "chain" refers to the one which leads to the simplest representation of the molecule.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

"Halo" and "halogen" refers to fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

"Haloalkoxy" indicates a haloalkyl group as defined herein attached through an oxygen bridge (oxygen of an alcohol radical).

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

"Heterocycloalkyl" is an alkyl group as defined herein substituted with a heterocyclo group as defined herein.

"Arylalkyl" is an alkyl group as defined herein substituted with an aryl group as defined herein.

"Heteroarylalkyl" is an alkyl group as defined herein substituted with a heteroaryl group as defined herein.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2, or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_{6-14}$ aryl. In certain embodiments, the aryl group is a substituted $C_{6-14}$ aryl. An aryl group may be optionally substituted with one or more functional groups that include but are not limited to, halo, hydroxy, nitro, amino, cyano, haloalkyl, aryl, heteroaryl, and heterocyclo.

The terms "AM ester" or "AM" as employed herein, by itself or as part of another group, refers to an acetoxymethyl ester of a carboxylic acid or a phenol.

The terms "amino" or "amine" include NH2, "monoalkylamine" or "monoalkylamino," and "dialkylamine" or "dialkylamino". The terms "monoalkylamine" and "monoalkylamino," "dialkylamine" and "dialkylamino as employed herein, by itself or as part of another group, refers to the group NH2 where one hydrogen has been replaced by alkyl group, as defined above.

The terms "dialkylamine" and "dialkylamino" as employed herein, by itself or as part of another group, refers to the group NH2 where both hydrogens have been replaced by alkyl groups, as defined above.

The term "heterocyclyl" (or "heterocyclo") includes saturated, and partially saturated heteroatom-containing ring radicals, where the heteroatoms may be selected from nitrogen, sulfur and oxygen. Heterocyclic rings comprise monocyclic 3-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may be optionally substituted, for example, with 1, 2, 3, 4 or more substituents that include but are not limited to, hydroxyl, Boc, halo, haloalkyl, cyano, alkyl, aralkyl, oxo, alkoxy, and amino. Examples of saturated heterocyclo groups include saturated 3- to 6-membered heteromonocyclic groups containing 1 to 4 nitrogen atoms [e.g., pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g., morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include but are not limited to, dihydrothienyl, dihydropyranyl, dihydrofuryl, and dihydrothiazolyl. Examples of partially saturated and saturated heterocyclo groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-12,4-triazolo[3,4-a]isoquinolyl, 3,4-dihydro-2H-benzo[1,4]oxazinyl, benzo[1,4]dioxanyl, 2,3-dihydro-1H-1Δ'-benzo[d]isothiazol-6-yl, dihydropyranyl, dihydrofuryl and dihydrothiazolyl.

Heterocyclo groups also include radicals where heterocyclic radicals are fused/condensed with aryl or heteroaryl radicals: such as unsaturated condensed heterocyclic group containing 1 to 5 nitrogen atoms, for example, indoline, isoindoline, unsaturated condensed heterocyclic group containing 1 to 2 oxygen atoms and 1 to 3 nitrogen atoms, unsaturated condensed heterocyclic group containing 1 to 2 sulfur atoms and 1 to 3 nitrogen atoms, and saturated, partially unsaturated and unsaturated condensed heterocyclic group containing 1 to 2 oxygen or sulfur atoms.

The term "heteroaryl" denotes aryl ring systems that contain one or more heteroatoms selected from O, N and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "optionally substituted" denotes the substitution of a group herein by a moiety including, but not limited to, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, $C_1$-$C_{12}$ heterocycloalkyl, $C_3$-$C_{12}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{10}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, azido, acyl, thioacyl, acyloxy, carboxyl, and carboxylic ester.

The term "substituted carboxy" refers to a carboxy ester, or carboxyamide, e.g., —C(O)R, where R is $NH_2$, substituted amino, alkoxy, aryloxy, heteroaryloxy, and substituted versions thereof.

The term "carbonyl" refers to a substitutent containing a group that is attached via a —C(O)—, e.g., carboxy, carboxy ester, carboxyamide, or aldehyde, and includes a —C(O)—R group where R can be OH, $NH_2$, substituted amino, O-alkyl, —O-aryl, O-heteroaryl, and substituted version thereof.

In one alternative embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g., with hydroxy, alkyl, alkoxy, halogen and amino. In certain embodiments "optionally substituted" includes one or more substituents independently selected from halogen, hydroxyl, amino, cyano, —CHO, —COOH, —$CONH_2$, alkyl including $C_1$-$C_6$ alkyl, alkenyl including $C_2$-$C_6$ alkenyl, alkynyl including $C_2$-$C_6$ alkynyl, —$C_1$-$C_6$ alkoxy, alkanoyl including $C_2$-$C_6$ alkanoyl, $C_1$-$C_6$ alkylester, (mono- and di-$C_1$-$C_6$ alkylamino) $C_0$-$C_2$ alkyl, haloalkyl including $C_1$-$C_6$ haloalkyl, hydoxy$C_1$-$C_6$ alkyl, ester, carbamate, urea, sulfonamide, —$C_1$-$C_6$ alkyl(heterocyclo), $C_1$-$C_6$ alkyl(heteroaryl), —$C_1$-$C_6$ alkyl($C_3$-$C_7$cycloalkyl), O—$C_1$-$C_6$ alkyl($C_3$-$C_7$cycloalkyl), $B(OH)_2$, phosphate, phosphonate and haloalkoxy including $C_1$-$C_6$ haloalkoxy.

When the term "substituted" appears prior or after a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups as defined herein.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "hydroxyalkyl" refers to the group HO-(alkyl)-.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound.

A compound of this disclosure may form a solvate with a solvent (including water). Therefore, in one non-limiting embodiment, the present disclosure includes a solvated form of the compound. The term "solvate" refers to a molecular complex of a compound (including a salt thereof) with one or more solvent molecules. Non-limiting examples of solvents are water, ethanol, isopropanol, dimethyl sulfoxide, acetone and other common organic solvents.

The term "hydrate" refers to a molecular complex comprising a compound and water. Pharmaceutically acceptable solvates in accordance with the invention include those wherein the solvent may be isotopically substituted, e.g., $D_2O$, $d_6$-acetone, $d_6$-DMSO. A solvate can be in a liquid or solid form.

Salts, solvates, hydrates, and prodrug forms of a compound are of interest. All such forms are embraced by the present disclosure. Thus, the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^1H$, $^2H$ (i.e., D) and $^3H$ (i.e., T), and reference to C is meant to include $^{12}C$ and all isotopes of carbon (such as $^{13}C$).

The term "heteroatom" as used herein, by itself or as part of another group, means an oxygen atom ("O"), a sulfur atom ("S") or a nitrogen atom ("N"). It will be recognized that when the heteroatom is nitrogen, it may form an $NR_1R_2$ moiety, where $R_1$ and $R_2$ are, independently from one another, hydrogen or alkyl, or together with the nitrogen to which they are bound, form a saturated or unsaturated 5-, 6-, or 7-membered ring.

The term "chelator", "chelate", "chelating group", "ionophore", or "ionophoric moiety" as used herein, by itself or as part of another group, refers to a chemical moiety that binds to, or complexes with, one or more metal ions, such as lithium, calcium, sodium, magnesium, potassium, and/or other biologically important metal ions. The binding affinity of a chelator for a particular metal ion can be determined by measuring the dissociation constant between that chelator and that ion. Chelators may include one or more chemical moieties that bind to, or complex with, a cation or anion. Examples of suitable chelators include crown ethers; azacrown ethers; succinic acid; citric acid; salicylic acids; histidines; imidazoles; ethyleneglycol-bis-(beta-aminoethyl ether) N,N'-tetraacetic acid (EGTA); nitroloacetic acid; acetylacetonate (acac); sulfate; dithiocarbamates; carboxylates; alkyldiamines; ethylenediamine (en); diethylenetriamine (dien); nitrate; nitro; nitroso; glyme; diglyme; bis (acetylacetonate)ethylenediamine (acacen); 1,2-bis(2-aminophenoxy)ethane-N,N,N',N'-tetraacetic acid (BAPTA), bipyridyl (bipy); terpyridyl (terpy); ethylenediaminetetraacetic acid (EDTA); 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (OTTA), 1,4,7-triazacyclononanetriacetic acid (NOTA), 1,4,8,11-tetraazacyclotetra-decanetetraacetic acid (TETA), DOTA-N-(2-aminoethyl) amide; DOTA-N-(2-aminophenethyl) amide; and 1,4,8,11-tetraazacyclotetradecane, among others.

The term "fluorophore or fluorophore moiety" as used herein, by itself or as part of another group, means a molecule or a portion of a molecule which exhibits fluorescence. By fluorescence is meant that the molecule or portion of a molecule can absorb excitation energy having a given wavelength and emit energy at a different wavelength. The intensity and wavelength of the emitted energy depend on the fluorophore, the chemical environment of the fluorophore, and the specific excitation energy used. Exemplary fluorophores include, but are not limited to, fluoresceins, rhodamines, coumarins, oxazines, cyanines, pyrenes, and other polycyclic aromatic molecules.

The term "xanthene", or "xanthene derivative", as used herein, by itself or as part of another group, means any compounds or substituents that contain one or more of the following fused ring structures or its derivatives:

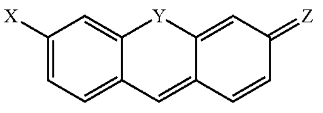

Xanthene (X, Z = O, S or Se or N; Y = O, S, Se, N, C, Si, P or B)

The term "fluorescein" as used herein, by itself or as part of another group, means any compounds or substituents that contain one or more of the following fused ring structures or its derivatives:

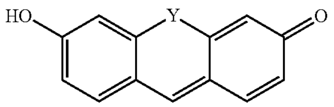

Fluorescein (Y = O, S, Se, N, C, Si, P or B, or substituted derivative thereof)

The term “fluorescein lactone” as used herein, by itself or as part of another group, means any compounds or substituents that contain one or more of the following fused ring structures or its derivatives:

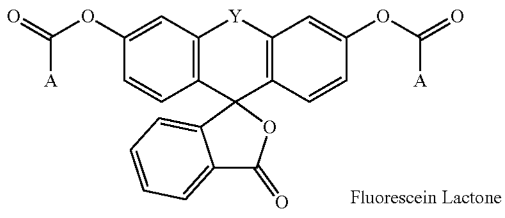

Fluorescein Lactone (Y = O, S, Se, N, C, Si, P or B, or substituted derivative thereof)

The term “pyrrole fluorophore”, or “pyrrole derivative”, as used herein, by itself or as part of another group, means any compounds or substituents that contain one or more of the following fused ring structures or its derivatives:

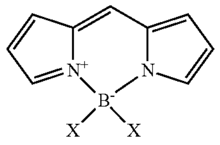

Pyrrole Fluorophore (X = F, CN, O or (-C≡C-)

The term “indicator compound” refers to the compounds of the invention, specifically to those compounds having utility as fluorescent metal ion indicators, as well as their acylated or otherwise protected precursor compounds, such as the acetoxymethyl ester derivatives suitable for adding to samples containing biological cells.

The term “screening” refers to the testing and/or evaluation of a multiplicity of molecules or compounds for a selected property or therapeutic utility. Screening is typically a repetitive, or iterative process. A multiplicity of candidate molecules may be screened for their ability to bind to a target molecule which is capable of denaturing and/or unfolding. For example, a multiplicity of candidate molecules may be evaluated for their ability to bind to a target molecule (e.g., a protein receptor) in a thermal shift assay. If none of a selected subset of molecules from the multiplicity of candidate molecules (for example, a combinatorial library) binds to the target molecule, then a different subset may be tested for binding in the thermal shift assay.

The term “high-throughput”, as used herein, encompasses screening activity in which human intervention is minimized, and automation is maximized. For example, high-throughput screening may include any of a variety of automated processes, including for example the automation of pipetting, mixing, and/or heating, the software-controlled generation of thermal unfolding information, and the software-controlled comparisons of thermal unfolding information. Alternatively, a high-throughput method is one in which hundreds of compounds can be screened per 24-hour period by a single individual operating a single suitable apparatus.

DETAILED DESCRIPTION OF THE PREFERRED EMBODIMENTS

The present application is directed to fluorescent dyes useful for preparing fluorescent metal ion indicators, the fluorescent indicators themselves, and the use of the fluorescent indicators for the detection, discrimination and quantification of metal cations.

In one aspect of this disclosure, the compounds may be described by Formula 1:

Formula 1

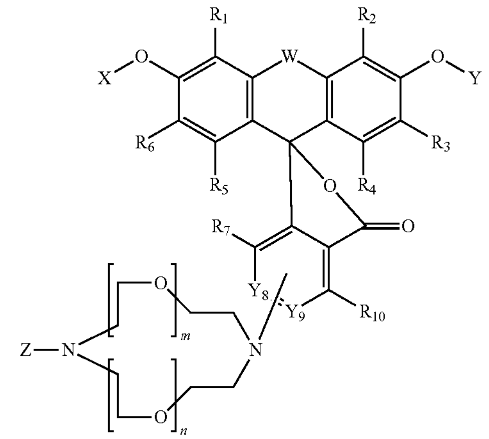

or a salt thereof, wherein:

$Y_8$ is $CR_8$ or C covalently bonded to N, and $Y_9$ is $CR_9$ or C covalently bonded to N, wherein one of $Y_8$ and $Y_9$ is C covalently bonded to the N;

$R_1$ to $R_{10}$ are independently selected from H, halogen, carboxy, substituted carboxy, alkyl, substituted alkyl, alkoxy, substituted alkoxy, aryloxy, substituted aryloxy, thiol, alkylthiol, arylthiol, azido, nitro, nitroso, cyano, amino, substituted amino, hydroxy, phosphonyl, sulfonyl, carbonyl, boronic acid, aryl, substituted aryl, heteroaryl, and substituted heteroaryl;

m and n are independently an integer from 0 to 3, wherein the sum of m+n is ≥2;

W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently selected from H, alkyl, substituted alkyl, aryl, substituted aryl, heteroaryl, and substituted heteroaryl;

X and Y are independently an acyl or substituted acyl; and

Z is substituted aryl.

In addition to the heteroatoms of the linked ionophore macrocycle, the compounds can include one, two, or more additional heteroatom-containing groups or substituents configured to coordinate a metal ion when bound. heteroatom-containing group can contain a nitrogen (e.g., amino) or oxygen (e.g., ether or hydroxyl) atom for coordination to a bound metal ion. In some aspects of Formula 1, one of $R_8$ and $R_9$ is a heteroatom-containing substituent capable of bonding to a chelated metal ion. In some aspects of Formula 1, $Y_8$ is $CR_8$ where $R_8$ is substituted with a heteroatom-containing substituent capable of bonding to a chelated metal ion. In some aspects of Formula 1, $Y_9$ is $CR_9$ where $R_9$ is substituted with a heteroatom-containing substituent capable of bonding to a chelated metal ion. The ionophore group of the compounds can be attached to either $Y_8$ or $Y_9$ via a N nitrogen atom of the macrocyclic ring.

In some aspects of Formula 1, $Y_9$ is covalently bonded to the N, and $R_8$ is alkoxy or substituted alkoxy. In some aspects of Formula 1, Ya is covalently bonded to the N, and $R_9$ is alkoxy or substituted alkoxy.

In some aspects of Formula 1, $R_1$, $R_2$, $R_4$, $R_5$, $R_7$ and $R_{10}$ are each H. In some aspects of Formula 1, $R_3$ and $R_6$ are independently halogen, aryl, substituted aryl, heteroaryl, substituted aryl, alkoxy, substituted alkoxy, or cyano.

In some aspects of Formula 1, $R_3$ and $R_6$ are independently fluoro, chloro, phenyl, pyridyl, $C_1$-$C_3$ alkoxy, cyano or aryl halide.

In some aspects of Formula 1, X and Y are independently $C_1$-$C_{10}$ acyl or $C_1$-$C_{10}$ acyloxymethyl.

In some aspects of Formula 1, Z is substituted aryl that is substituted with a heteroatom-containing substituent configured, and capable of bonding to a chelated metal ion. In some aspects of Formula 1, Z is substituted aryl that is substituted, e.g., at the alpha position (i.e., adjacent to the nitrogen of the ionophore macrocycle attached to Z), with a heteroatom-containing substituent capable of bonding to a chelated metal ion. In some aspects of Formula 1, Z is alkoxyaryl. In some aspects, the alkoxyaryl is 2'-alkoxyaryl. In some aspects of Formula 1, Z is ($C_1$-$C_6$)alkoxy-phenyl. In some aspects, the ($C_1$-$C_6$)alkoxy-phenyl is 2'-methoxyphenyl.

In some aspects of Formula 1, the ionophore macrocyclic ring size is selected based on the target ion. In some aspects of Formula 1, the sum of m+n is 2. In some aspects of Formula 1, the sum of m+n is 3. In some aspects of Formula 1, the sum of m+n is 4. In some aspects of Formula 1, m and n are each 1. In some aspects of Formula 1, m and n are each 2. In some aspects of Formula 1, m is 1, and n is 2.

In some aspects of Formula 1, $R_1$-$R_{10}$ are independently selected from H, halogen, carboxy, substituted carboxy, alkoxy, aryloxy, thiol, alkylthiol, arylthiol, azido, nitro, nitroso, cyano, amino, hydroxy, phosphonyl, sulfonyl, a carbonyl, boronic acid, optionally substituted aryl, optionally substituted heteroaryl, optionally substituted alkyl, and optionally substituted alkoxy, wherein substituted aryl, substituted heteroaryl, substituted alkyl, and substituted alkoxy are substituted with one or more substituents selected from halogen, amino, hydroxy, phosphonyl, sulfonyl, a carbonyl, boronic acid, aryl, and heteroaryl.

In some aspects of Formula 1, the Ya is C covalently bonded to a N of the ionophore. In one aspect of Formula 1, the compounds may be described by Formula 2:

Formula 2

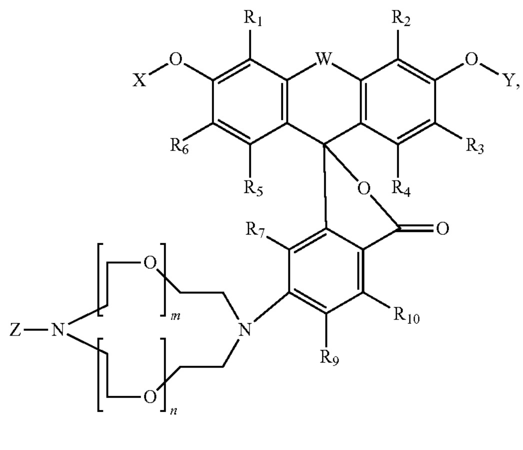

or a salt thereof.

In some aspects of Formula 2, $R_1$-$R_7$, $R_9$ and $R_{10}$ are independently selected from H, halogen, carboxy, substituted carboxy, alkyl, substituted alkyl, alkoxy, substituted alkoxy, thiol, azido, nitro, nitroso, cyano, amino, hydroxy, phosphonyl, sulfonyl, a carbonyl, boronic acid, aryl, substituted aryl, heteroaryl, and substituted heteroaryl; m and n are independently an integer from 0 to 3, wherein the sum of m+n is ≥2;

W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently selected from H, alkyl, substituted alkyl, aryl, substituted aryl, heteroaryl, and substituted heteroaryl;

X and Y are independently an acyl or substituted acyl; and Z is aryl or substituted aryl.

In some aspects of this disclosure, the compound is of Formula 2, wherein: $R_1$-$R_7$, $R_9$ and $R_{10}$ are independently H, halogen, carboxy, substituted carboxy, alkyl, alkoxy, aryloxy, thiol, alkylthiol, arylthiol, azido, nitro, nitroso, cyano, amino, hydroxy, phosphonyl, sulfonyl, a carbonyl, boronic acid, aryl or heteroaryl; alkyl, or alkoxy that is itself optionally substituted one or more times by halogen, amino, hydroxy, phosphonyl, sulfonyl, a carbonyl, boronic acid, aryl or heteroaryl; m and n are independently 0, 1, 2 or 3, wherein the sum of m+n is 2, 3 or 4; W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently selected from H, alkyl, aryl, or heteroaryl; X and Y are independently an acyl or an acyloxymethyl having 1-10 carbons; and Z is a 2'-alkoxyaryl.

In some aspects of this disclosure, the compound is of Formula 2, wherein: $R_1$-$R_7$, $R_9$ and $R_{10}$ are independently H, chloro, fluoro, carboxy, substituted carboxy, alkoxy, aryloxy, aryl or heteroaryl; m and n are independently 0, 1, 2 or 3, wherein the sum of m+n is 2, 3 or 4; W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently selected from alkyl, aryl, or heteroaryl; X and Y are independently a $C_1$-$C_{10}$ acyl or a $C_1$-$C_{10}$ acyloxymethyl; and Z is a 2'-alkoxyaryl.

In some aspects of this disclosure, the compound is of Formula 2, wherein: $R_1$-$R_7$, $R_9$ and $R_{10}$ are independently H, alkyl, chloro, fluoro, alkoxy, aryloxy, aryl or heteroaryl; m and n are independently 1 or 2; W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently selected from alkyl, aryl, or heteroaryl; X and Y are independently acetyl or acetoxymethyl; and Z is a 2'-alkoxyaryl.

In yet another aspect of Formula 2, the compounds of this disclosure may be described by Formula 2A:

Formula 2A

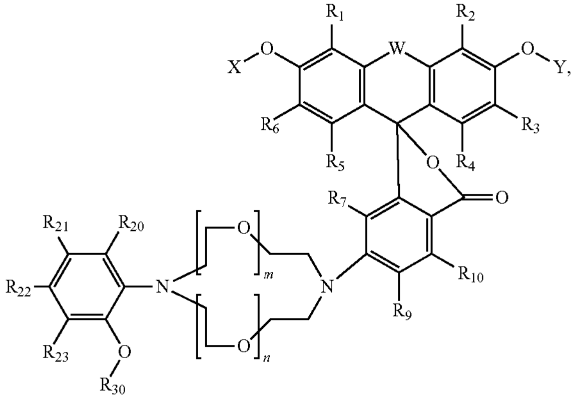

or a salt thereof, where $R_{20}$-$R_{23}$ are independently H, alkyl, halogen, carboxy, substituted carboxy, alkoxy, aryloxy, alkylthiol, arylthiol, azido, cyano, a carbonyl, aryl, heteroaryl or substituted version thereof, and $R_{30}$ is H, alkyl, substituted alkyl, aryl, substituted aryl, heteroaryl or substituted heteroaryl.

In some embodiments, the compound is of Formula 2A, wherein: $R_{20}$-$R_{23}$ are independently H, alkyl, halogen, carboxy, substituted carboxy, alkoxy, aryloxy, alkylthiol, arylthiol, azido, cyano, a carbonyl, aryl or heteroaryl; and $R_{30}$ is alkyl, aryl, or heteroaryl.

In some embodiments, the compound is of Formula 2A, wherein: $R_1$-$R_7$, $R_9$, $R_{10}$ and $R_{20}$-$R_{23}$ are independently H, alkyl, halogen, carboxy, substituted carboxy, alkoxy, aryloxy, alkylthiol, arylthiol, azido, cyano, a carbonyl, aryl or heteroaryl; $R_{30}$ is alkyl; m and n are independently an integer from 0 to 3, where the sum of m+n is 2, 3 or 4; W is O, N—$R_{31}$, C($R_{31}R_{32}$), Si($R_{31}R_{32}$), S═O, O═S═O, P—$R_{32}$, O═P—$R_{32}$, O ═P—O$R_{32}$, or B(O$R_{31}$), wherein $R_{31}$ and $R_{32}$ are independently alkyl, aryl, or heteroaryl; and X and Y are independently acetyl or acetoxymethyl.

In yet another aspect of this disclosure, the compound is of Formula 2A wherein $R_1$-$R_7$, $R_9$, $R_{10}$, and $R_{20}$-$R_{23}$ are independently H, alkyl, chloro, fluoro, alkoxy, aryloxy, cyano, aryl or heteroaryl; m and n are an integer from 0 to 3, and the sum of m+n is 2, 3 or 4; W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently methyl, ethyl, a propyl, a butyl, a benzyl, a phenyl, or a pyridyl; X and Y are independently acetyl or acetoxymethyl.

In yet another aspect of this disclosure, the compound is of Formula 2A wherein $R_1$-$R_7$, $R_9$, $R_{10}$, and $R_{20}$-$R_{23}$ are independently H, alkyl, chloro, fluoro, alkoxy, aryloxy, aryl or heteroaryl; m and n are an integer from 0 to 3, and the sum of m+n is 2, 3 or 4; W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently methyl, ethyl, a propyl, a butyl, a benzyl, a phenyl, or a pyridyl; X and Y are independently acetyl or acetoxymethyl; at least one of $R_7$ and $R_9$ is alkoxy or aryloxy.

In some aspects of this disclosure, the compound is of Formula 2A wherein: $R_1$-$R_7$, $R_9$, $R_{10}$, and $R_{20}$-$R_{23}$ are independently H, alkyl, chloro, fluoro, alkoxy, aryloxy, aryl or heteroaryl; m and n are independently 1 or 2; W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently methyl, ethyl, a propyl, a butyl, a benzyl, a phenyl, or a pyridyl; and X and Y are independently acetyl or acetoxymethyl.

In some aspects of this disclosure, the compound is of Formula 2A wherein at least one of $R_7$ and $R_9$ is alkoxy or aryloxy. In some aspects, at least one of $R_7$ and $R_9$ is ($C_1$-$C_6$)alkoxy, such as methoxy. In some aspects, at least one of $R_7$ and $R_9$ is aryloxy, such as phenoxy.

In some aspects of Formula 1, the $Y_9$ is C covalently bonded to N. In one aspect of this disclosure, the compounds may be described by Formula 3:

Formula 3

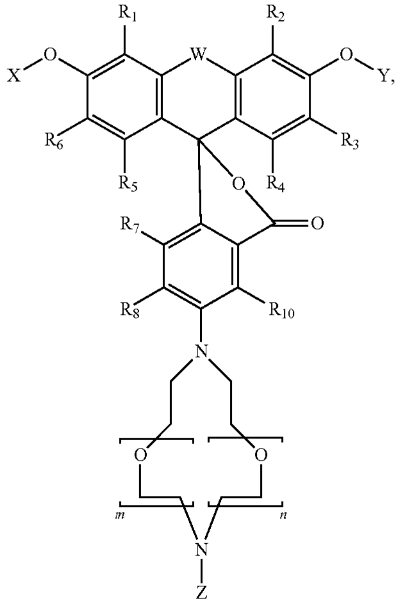

or a salt thereof.

In some embodiments, the compound is of Formula 3, wherein:

- $R_1$-$R_8$, and $R_{10}$ are independently selected from H, halogen, carboxy, substituted carboxy, alkyl, substituted alkyl, alkoxy, substituted alkoxy, thiol, azido, nitro, nitroso, cyano, amino, hydroxy, phosphonyl, sulfonyl, a carbonyl, boronic acid, aryl, substituted aryl, heteroaryl, and substituted heteroaryl;
- m and n are independently an integer from 0 to 3, wherein the sum of m+n is ≥2;
- W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently selected from H, alkyl, substituted alkyl, aryl, substituted aryl, heteroaryl, and substituted heteroaryl;
- X and Y are independently an acyl or substituted acyl; and
- Z is aryl or substituted aryl.

In some embodiments of Formula 3, $R_1$-$R_8$, and $R_{10}$ are independently H, halogen, carboxy, substituted carboxy, alkyl, alkoxy, aryloxy, thiol, alkylthiol, arylthiol, azido, nitro, nitroso, cyano, amino, hydroxy, phosphonyl, sulfonyl, a carbonyl, boronic acid, aryl or heteroaryl; alkyl, or alkoxy that is itself optionally substituted one or more times by halogen, amino, hydroxy, phosphonyl, sulfonyl, a carbonyl, boronic acid, aryl or heteroaryl; m and n are an integer from 0 to 3, and the sum of m+n is ≥2; W is O, N—$R_{31}$, C($R_{31}R_{32}$), Si($R_{31}R_{32}$), S═O, O═S═O, P—$R_{32}$, O═P—$R_{32}$, O═P—$OR_{32}$, or B($OR_{31}$), wherein $R_{31}$ and $R_{32}$ are independently selected from H, alkyl, aryl, or heteroaryl; X and Y are independently an acyl or an acyloxymethyl having 1-10 carbons; and Z is a 2'-alkoxyaryl.

In some aspects, the compound is of Formula 3, wherein:

$R_1$-$R_8$, and $R_{10}$ are independently H, chloro, fluoro, carboxy, substituted carboxy, alkoxy, aryloxy, aryl or heteroaryl;

m and n are independently 0, 1, 2 or 3, wherein the sum of m+n is 2, 3 or 4;

W is O, N—$R_{31}$, C($R_{31}R_{32}$), Si($R_{31}R_{32}$), S═O, O═S═O, P—$R_{32}$, O═P—$R_{32}$, O═P—$OR_{32}$, or B($OR_{31}$), wherein $R_{31}$ and $R_{32}$ are independently selected from H, alkyl, aryl, or heteroaryl;

X and Y are independently a $C_1$-$C_{10}$ acyl or a $C_1$-$C_{10}$ acyloxymethyl; and Z is a 2'-alkoxyaryl.

In some aspects, the compound is of Formula 3, wherein:

$R_1$-$R_8$, and $R_{10}$ are independently H, alkyl, chloro, fluoro, alkoxy, aryloxy, aryl or heteroaryl;

m and n are independently 1 or 2;

W is O, N—$R_{31}$, C($R_{31}R_{32}$), Si($R_{31}R_{32}$), S═O, O═S═O, P—$R_{32}$, O═P—$R_{32}$, O═P—$OR_{32}$, or B($OR_{31}$), wherein $R_{31}$ and $R_{32}$ independently selected from alkyl, aryl, or heteroaryl;

X and Y are independently acetyl or acetoxymethyl; and

Z is a 2'-alkoxyaryl.

In some aspects, Z is 2'-methoxyphenyl.

In some aspects of Formula 3, the compounds of this disclosure may be described by Formula 3A:

Formula 3A

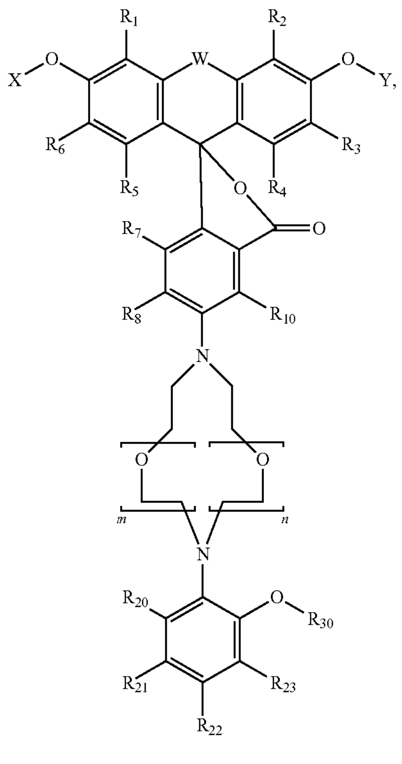

or a salt thereof, wherein:

$R_{20}$-$R_{23}$ are independently H, alkyl, substituted alkyl, halogen, carboxy, substituted carboxy, alkoxy, substituted alkoxy, azido, cyano, a carbonyl, aryl, substituted aryl, heteroaryl, or substituted heteroaryl; and $R_{30}$ is alkyl, substituted alkyl, aryl, substituted aryl, heteroaryl or substituted heteroaryl.

In some embodiments of Formula 3A, $R_{20}$-$R_{23}$ are independently H, alkyl, halogen, carboxy, substituted carboxy, alkoxy, aryloxy, alkylthiol, arylthiol, azido, cyano, a carbonyl, aryl or heteroaryl; and $R_{30}$ is alkyl, aryl, or heteroaryl.

In some embodiments of Formula 3A, $R_1$-$R_8$, $R_{10}$ and $R_{20}$-$R_{23}$ are independently H, alkyl, halogen, carboxy, substituted carboxy, alkoxy, aryloxy, alkylthiol, arylthiol, azido, cyano, a carbonyl, aryl or heteroaryl; $R_{30}$ is alkyl; m and n are independently an integer from 0 to 3, where the sum of m+n is 2, 3 or 4; W is O, N—$R_{31}$, C($R_{31}R_{32}$), Si($R_{31}R_{32}$), S═O, O═S═O, P—$R_{32}$, O═P—$R_{32}$, O═P—$OR_{32}$, or B($OR_{31}$), wherein $R_{31}$ and $R_{32}$ are independently alkyl, aryl, or heteroaryl; and X and Y are independently acetyl or acetoxymethyl.

In yet another aspect of this disclosure, the compound is of Formula 3A wherein $R_1$-$R_8$, $R_{10}$ and $R_{20}$-$R_{23}$ are independently H, alkyl, chloro, fluoro, alkoxy, aryloxy, cyano, aryl or heteroaryl; m and n are an integer from 0 to 3, and the sum of m+n is 2, 3 or 4; W is O, N—$R_{31}$, C($R_{31}R_{32}$), Si($R_{31}R_{32}$), S═O, O═S═O, P—$R_{32}$, O═P—$R_{32}$, O═P—$OR_{32}$, or B($OR_{31}$), wherein $R_{31}$ and $R_{32}$ are independently methyl, ethyl, a propyl, a butyl, a benzyl, a phenyl, or a pyridyl; and X and Y are independently acetyl or acetoxymethyl.

In yet another aspect of this disclosure, the compound is of Formula 3A wherein $R_1$-$R_8$, $R_{10}$ and $R_{20}$-$R_{23}$ are independently H, alkyl, chloro, fluoro, alkoxy, aryloxy, aryl or heteroaryl; m and n are an integer from 0 to 3, where the sum of m+n is 2, 3 or 4; W is O, N—$R_{31}$, C($R_{31}R_{32}$), Si($R_{31}R_{32}$), S═O, O═S═O, P—$R_{32}$, O═P—$R_{32}$, O═P—$OR_{32}$, or B($OR_{31}$), wherein $R_{31}$ and $R_{32}$ are independently methyl, ethyl, propyl, butyl, benzyl, phenyl, or a pyridyl; X and Y are independently acetyl or acetoxymethyl; at least one of $R_8$ and $R_{10}$ is alkoxy or aryloxy.

In some aspects of this disclosure, the compound is of Formula 3 or 3A wherein at least one of $R_8$ and $R_{10}$ is alkoxy or aryloxy. In some aspects, at least one of $R_8$ and $R_{10}$ is ($C_1$-$C_6$)alkoxy, such as methoxy. In some aspects, at least one of $R_8$ and $R_{10}$ is aryloxy, such as phenoxy.

In yet another aspect of this disclosure, the compounds of this disclosure may be described by Formula 4:

Formula 4

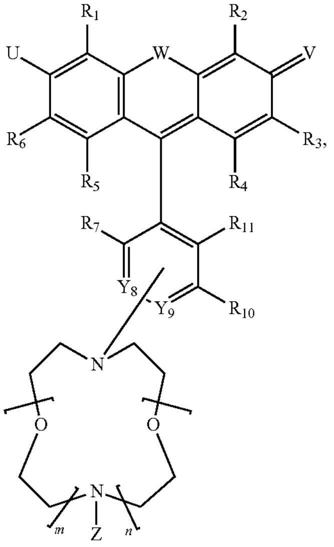

or a salt thereof, wherein:

$Y_8$ is $CR_8$ or C covalently bonded to N, and $Y_9$ is $CR_9$ or C covalently bonded to N, wherein one of $Y_8$ and $Y_9$ is C covalently bonded to the N;

$R_1$-$R_{11}$ are independently H, alkyl, substituted alkyl, halogen, carboxy, substituted carboxy, alkoxy, substituted alkoxy, azido, cyano, a carbonyl, aryl, substituted aryl, heteroaryl, or substituted heteroaryl, wherein one of $R_7$ and $R_{11}$ is carboxy, substituted carboxy, alkyl, substituted alkyl, alkoxy, or substituted alkoxy;

m and n are independently an integer from 0 to 3, wherein the sum of m+n is ≥2;

U is OH, or $NR_{35}R_{36}$, and V is O, or $+NR_{35}R_{36}$, wherein $R_{35}$ and $R_{36}$ are independently H, alkyl, substituted alkyl, aryl, substituted aryl, heteroaryl, or substituted heteroaryl, or each $R_{35}$ and $R_{36}$ are cyclically linked with $R_1$ or $R_6$, or $R_2$ or $R_3$, respectively, to form two fused 6-membered heterocycles (e.g., fused piperidine);

W is O, N—$R_{31}$, $C(R_{31}R_{32})$, $Si(R_{31}R_{32})$, S═O, O═S═O, P—$R_{32}$, O═P—$R_{32}$, O═P—$OR_{32}$, or $B(OR_{31})$, wherein $R_{31}$ and $R_{32}$ are independently H, alkyl, substituted alkyl, aryl, substituted aryl, heteroaryl, or substituted heteroaryl; and Z is aryl or substituted aryl.

In some aspects of Formula 4, one of $R_7$ and $R_{11}$ is carboxy, or substituted carboxy. In some aspects of Formula 4, one of $R_7$ and $R_{11}$ is $CO_2H$. In some aspects of Formula 4, one of $R_7$ and $R_{11}$ is $CO_2R_{21}$, where $R_{21}$ is alkyl or substituted alkyl.

In some aspects of Formula 4, $R_1$-$R_{11}$ are independently H, alkyl, halogen, carboxy, substituted carboxy, alkoxy, aryloxy, alkylthiol, arylthiol, azido, cyano, a carbonyl, aryl or heteroaryl; and one of $R_7$ and $R_8$ is a carboxy, substituted carboxy, alkyl, or alkoxy.

In some aspects of Formula 4:

$Y_9$ is C covalently bonded to N;

$R_{11}$ is a carboxy, or substituted carboxy;

$R_7$, and $R_{10}$, $R_1$, $R_2$, $R_4$ and $R_5$ are each H;

$R_3$ and $R_6$ are independently halogen, aryl, substituted aryl, heteroaryl, substituted aryl, alkoxy, substituted alkoxy, or cyano; and $R_8$ is alkoxy or substituted alkoxy.

In some aspects of Formula 4:

$Y_8$ is C covalently bonded to N;

$R_{11}$ is a carboxy, or substituted carboxy;

$R_7$, and $R_{10}$, $R_1$, $R_2$, $R_4$ and $R_5$ are each H;

$R_3$ and $R_6$ are independently halogen, aryl, substituted aryl, heteroaryl, substituted aryl, alkoxy, substituted alkoxy, or cyano; and $R_9$ is alkoxy or substituted alkoxy.

In some aspects of Formula 4:

$Y_9$ is covalently bonded to $N_1$;

$R_{11}$ is a carboxy, or substituted carboxy;

$R_7$, and $R_8$, $R_1$, $R_2$, $R_4$, and $R_5$ are each H;

$R_3$ and $R_6$ are independently halogen, aryl, substituted aryl, heteroaryl, substituted aryl, alkoxy, substituted alkoxy, or cyano; and $R_{10}$ is alkoxy or substituted alkoxy.

In some aspects of Formula 4, U is OH; and V is O. In some aspects of Formula 4: U is $NR_{35}R_{36}$; and V is $+NR_{35}R_{36}$, where $R_{35}$ and $R_{36}$ are independently alkyl, or substituted alkyl.

In some aspects of Formula 4, Z is alkoxyaryl. In some aspects of Formula 4, the alkoxyaryl is 2'-alkoxyaryl, such as 2-methoxyphenyl.

In some aspects of Formula 4, the compounds of this disclosure may be described by Formula 5:

Formula 5

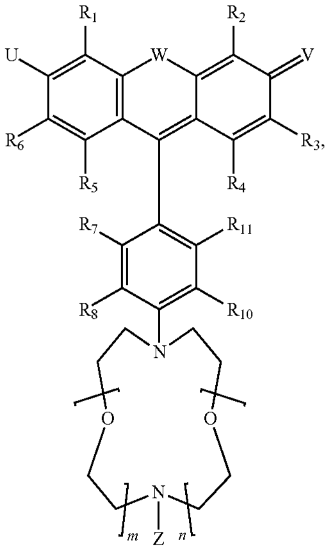

or a salt thereof.

In some aspects of Formula 4 or 5, the compounds of this disclosure may be described by Formula 5A:

Formula 5A

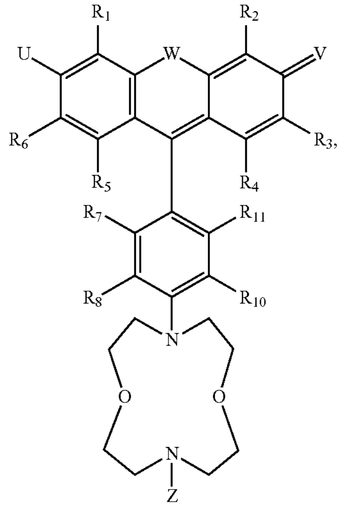

or a salt thereof.

In some embodiments of Formula 5-5A, $R_1$-$R_8$, $R_{10}$ and $R_{11}$ are independently H, alkyl, halogen, carboxy, substituted carboxy, alkoxy, aryloxy, alkylthiol, arylthiol, azido, cyano, a carbonyl, aryl or heteroaryl; one of $R_7$ and $R_8$ is a carboxy, carboxyl derivative, alkyl, or alkoxy while the other one is H, alkyl, halogen, carboxy, substituted carboxy, alkoxy, aryloxy, alkylthiol, arylthiol, azido, cyano, a carbonyl, aryl or heteroaryl; U is OH, $NH_2$, $NHR_{35}$ or $NR_{35}R_{36}$ wherein $R_{35}$ and $R_{36}$ are independently an alkyl; V is O, $+NH_2$, $+NHR_{35}$ or $+NR_{35}R_{36}$ wherein $R_{35}$ and $R_{36}$ are independently an alkyl; W is O, N—$R_{31}$, C($R_{31}R_{32}$), Si($R_{31}R_{32}$), S═O, O═S═O, P—$R_{32}$, O═P—$R_{32}$, O═P—$OR_{32}$, or B($OR_{31}$), wherein $R_{31}$ and $R_{32}$ are independently H, alkyl, aryl, or heteroaryl; and Z is a 2'-alkoxyaryl.

In yet another aspect of this disclosure the compounds are of Formula 5-5A, wherein $R_1$-$R_8$, $R_{10}$ and $R_{11}$ are independently H, alkyl, chloro, fluoro, alkoxy, cyano, aryl, aryloxy or heteroaryl; W is O, C($R_{31}R_{32}$), or Si($R_{31}R_{32}$), wherein $R_{31}$ and $R_{32}$ are independently methyl, ethyl, a propyl, a butyl, a benzyl, a phenyl, or a pyridyl; and Z is a 2'-methoxyphenyl, 2'-ethoxyphenyl or 2'-carboxymethoxyphenyl.

In yet another aspect of this disclosure the compounds are of Formula 5-5A, wherein $R_1$-$R_8$, $R_{10}$ and $R_{11}$ are independently H, alkyl, halogen, cyano, alkoxy, aryloxy, aryl or heteroaryl; $R_{11}$ is a carboxy, methyl or methoxy; $R_7$ is H; U is OH, $NH_2$, $NHR_{35}$ or $NR_{35}R_{36}$ wherein $R_{35}$ and $R_{36}$ are independently alkyl, aryl, or heteroaryl; V is O, $+NH_2$, $+NHR_{35}$ or $+NR_{35}R_{36}$ wherein $R_{35}$ and $R_{36}$ are independently alkyl, aryl, or heteroaryl; W is O, C($R_{31}R_{32}$), or Si($R_{31}R_{32}$) wherein $R_{31}$ and $R_{32}$ are independently alkyl, aryl, or heteroaryl; and at least one of $R_8$ and $R_{10}$ is alkoxy or aryloxy.

In some aspects of Formula 5-5A, one of $R_7$ and $R_{11}$ is a carboxy, a carboxyl ester, carboxamide or alkyl, and the other is H or alkyl.

In some aspects of Formula 5-5A, Z is aryl or substituted aryl. In some aspects of Formula 5-5A, Z is 2'-methoxyphenyl, 2'-ethoxyphenyl or 2'-carboxymethoxyphenyl.

In some aspects of Formula 5, the ionophore macrocyclic ring size is selected based on the target ion. In some aspects of Formula 5, the sum of m+n is 2. In some aspects of Formula 5, the sum of m+n is 3. In some aspects of Formula 5, the sum of m+n is 4. In some aspects of Formula 5, m and n are each 1. In some aspects of Formula 5, m and n are each 2. In some aspects of Formula 5, m is 1, and n is 2.

In some aspects of Formula 5, the compounds of this disclosure may be described by Formula 6:

Formula 6

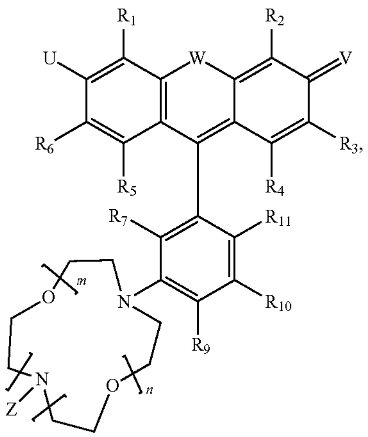

or a salt thereof.

In some aspects of Formula 6, the compounds of this disclosure may be described by Formula 6A:

Formula 6A

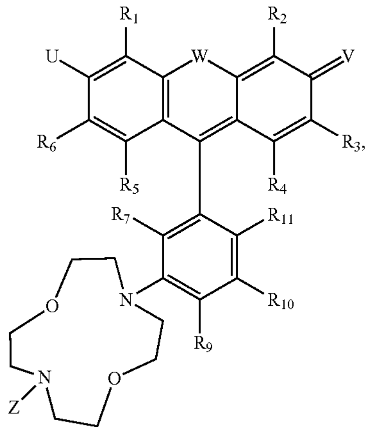

or a salt thereof.

In some embodiments of Formula 6-6A, $R_1$-$R_7$, $R_9$ and $R_{10}$ are independently H, alkyl, halogen, carboxy, substituted carboxy, alkoxy, aryloxy, alkylthiol, arylthiol, azido, cyano, a carbonyl, aryl or heteroaryl; one of $R_7$ and $R_{11}$ is carboxy, carboxyl derivative, alkyl, or alkoxy, while the other one is H, alkyl, halogen, carboxy, substituted carboxy, alkoxy, aryloxy, alkylthiol, arylthiol, azido, cyano, a carbonyl, aryl or heteroaryl; U is OH, $NH_2$, $NHR_{35}$ or $NR_{35}R_{36}$, wherein $R_{35}$ and $R_{36}$ are independently alkyl, aryl, or heteroaryl; V is O, $+NH_2$, $+NHR_{35}$ or $+NR_{35}R_{36}$, wherein $R_{35}$ and $R_{36}$ are independently alkyl, aryl, or heteroaryl; W is O, N—$R_{31}$, C($R_{31}R_{32}$), Si($R_{31}R_{32}$), S═O, O═S═O, P—$R_{32}$, O═P—$R_{32}$, O═P—$OR_{32}$, or B($OR_{31}$), wherein $R_{31}$ and $R_{32}$ are independently H, alkyl, aryl, or heteroaryl; and Z is a 2'-alkoxyaryl.

In yet another aspect of this disclosure the compounds are of Formula 6-6A, wherein $R_1$-$R_6$, and $R_9$-$R_{11}$ are independently H, alkyl, chloro, fluoro, alkoxy, cyano, aryl, aryloxy or heteroaryl; W is O, $C(R_{31}R_{32})$, $Si(R_{31}R_{32})$, O═P—$R_{32}$, or O═P—$OR_{32}$, wherein $R_{31}$ and $R_{32}$ are independently methyl, ethyl, a propyl, a butyl, a benzyl, a phenyl, or a pyridyl; and Z is a 2'-methoxyphenyl, 2'-ethoxyphenyl or 2'-carboxymethoxyphenyl.

In yet another aspect of this disclosure the compounds are of Formula 6-6A, wherein $R_1$-$R_6$, and $R_9$-$R_{11}$ are independently H, alkyl, halogen, cyano, alkoxy, aryloxy, aryl or heteroaryl; $R_7$ is a carboxy, methyl or methoxy; $R_{11}$ is H; U is OH, $NH_2$, $NHR_{35}$ or $NR_{35}R_{36}$, wherein $R_{35}$ and $R_{36}$ are independently alkyl, aryl, or heteroaryl; V is O, $+NH_2$, $+NHR_{35}$ or $+NR_{35}R_{36}$, wherein $R_{35}$ and $R_{36}$ are independently alkyl, aryl, or heteroaryl; W is O, $C(R_{31}R_{32})$, or $Si(R_{31}R_{32})$, wherein $R_{31}$ and $R_{32}$ are independently alkyl, aryl, or heteroaryl; at least one of $R_7$ and $R_9$ is alkoxy or aryloxy.

In some aspects of Formula 6-6A, one of $R_7$ and $R_{11}$ is a carboxy, a carboxyl ester, carboxamide or alkyl, and the other is H or alkyl.

In some aspects of Formula 6-6A, Z is aryl or substituted aryl. In some aspects of Formula 6-6A, Z is 2'-methoxyphenyl, 2'-ethoxyphenyl or 2'-carboxymethoxyphenyl.

In some aspects of Formula 6, the ionophore macrocyclic ring size is selected based on the target ion. In some aspects of Formula 6, the sum of m+n is 2. In some aspects of Formula 6, the sum of m+n is 3. In some aspects of Formula 6, the sum of m+n is 4. In some aspects of Formula 6, m and n are each 1. In some aspects of Formula 6, m and n are each 2. In some aspects of Formula 6, m is 1, and n is 2.

In some aspects of Formula 4-6A, U is $NR_{35}R_{36}$, and V is $+NR_{35}R_{36}$, where $R_{35}$ and $R_{36}$ are independently H, alkyl, substituted alkyl, aryl, substituted alkyl, heteroaryl, or substituted heteroaryl. For example, as shown in the example compound 38, where $R_{35}$ and $R_{36}$ are each methyl.

In some aspects of Formula 4-6A, U is $NR_{35}R_{36}$, and V is $+NR_{35}R_{36}$, where each $R_{35}$ and $R_{36}$ are each cyclically linked with $R_1$ or $R_6$, or $R_2$ or $R_3$, respectively, to form fused 6-membered heterocycles (e.g., fused piperidine).

For example, as shown in the example compound 39 where the fused 6-membered heterocycles are four fused piperidine derivatives.

The fluorophore moiety can be any compound described by any of Formulas 1 to 6A that exhibits an absorption maximum beyond 450 nm, that is bound to a chelator by a covalent linkage L, or that is fused to a chelator. The covalent linkage L may be a single covalent bond, or a suitable combination of stable chemical bonds, as described in greater detail below. The covalent linkage binding the fluorophore moiety to the chelator is typically a single bond, but optionally incorporates 1-20 nonhydrogen atoms selected from the group consisting of C, N, O, P, and S.

As described above, where the fluorophore moiety is a xanthene, the resulting compound may be a fluorescein, a rhodol (U.S. Pat. No. 5,227,487, hereby incorporated by reference), or a rhodamine. As used herein, fluorescein includes benzo- or dibenzofluoresceins, seminaphthofluoresceins, or naphthofluoresceins. Similarly, as used herein rhodol includes seminaphthorhodafluors (U.S. Pat. No. 4,945,171, hereby incorporated by reference). Fluorinated xanthene dyes have been described previously as possessing particularly useful fluorescence properties (U.S. Pat. No. 6,162,931, hereby incorporated by reference).

In yet another aspect of this disclosure, the compounds of this disclosure may be described by Formula 7:

Formula 7

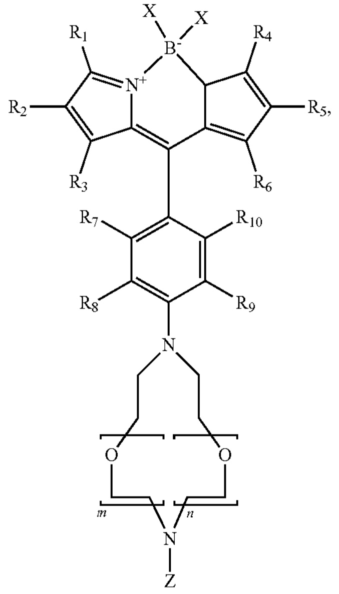

or a salt thereof.

In this embodiment, $R_1$-$R_{10}$ are independently H, alkyl, halogen, carboxy, substituted carboxy, alkoxy, aryloxy, alkylthiol, arylthiol, azido, cyano, a carbonyl, aryl or heteroaryl; m and n are an integer from 0 to 3, and the sum of m+n is ≥2; X is F, cyano, an alkynyl or $OR_{11}$ wherein $R_{11}$ is alkyl, aryl, or heteroaryl; Z is a 2'-alkoxyaryl.

In yet another aspect of this disclosure, the compounds of Formula 7 wherein one or more of $R_1$ and $R_2$, $R_2$ and $R_3$, $R_4$ and $R_5$, $R_5$ and $R_6$, $R_7$ and $R_8$, or $R_9$ and $R_{10}$, may together with the atoms to which they are attached, independently form a fused cyclic group, such as a fused aryl or heteroaryl. In some aspects of Formula 7, one or more of $R_1$ and $R_2$, $R_2$ and $R_3$, $R_4$ and $R_5$, $R_5$ and $R_6$, $R_7$ and $R_8$, and $R_9$ and $R_{10}$, together with the atoms to which they are attached form a fused cyclic group selected from cycloalkyl, substituted cycloalkyl, heterocycle, substituted heterocycle, heteroaryl, and substituted heteroaryl.

In yet another aspect of this disclosure, the compounds of Formula 7 wherein $R_1$-$R_{10}$ are independently H, alkyl, chloro, fluoro, alkoxy, aryloxy, cyano, aryl or heteroaryl; X is F; At least one of $R_8$ and $R_9$ is alkoxy or aryloxy.

In some aspects of Formula 7, the ionophore macrocyclic ring size is selected based on the target ion. In some aspects of Formula 7, the sum of m+n is 2. In some aspects of Formula 7, the sum of m+n is 3. In some aspects of Formula 7, the sum of m+n is 4. In some aspects of Formula 7, m and n are each 1. In some aspects of Formula 7, m and n are each 2. In some aspects of Formula 7, m is 1, and n is 2.

In one aspect of this disclosure, the fluorophore moiety has an absorption maximum beyond 480 nm. In a particularly useful embodiment, the fluorophore moiety absorbs at or near 488 nm to 514 nm, and so is particularly suitable for excitation by the output of an argon-ion laser excitation source, or near 546 nm, and so is particularly suitable for excitation by a mercury arc lamp.

The fluorophore moiety is typically selected to confer its fluorescence properties on the indicator compound it is incorporated into. That is, the resulting indicator compound exhibits a detectable optical response when excited by energy having a wavelength at which that fluorophore absorbs as used herein, a detectable optical response means a change in, or occurrence of, an optical property that is detectable either by observation or instrumentally, such a change in absorption (excitation) wavelength, fluorescence emission wavelength, fluorescence emission intensity, fluorescence polarization, or fluorescence lifetime, among others.

In addition, the compounds of this disclosure preferably exhibit a detectable change in the optical response upon binding a target metal ion. Where the detectable response is a fluorescence response, the detectable change is typically a change in fluorescence, such as a change in the intensity, excitation or emission wavelength distribution of fluorescence, fluorescence lifetime, fluorescence polarization, or a combination thereof. Preferably, the change in optical response upon binding the target metal ion is a change in fluorescence intensity that is greater than approximately 5-fold, more preferably greater than 10-fold.

Synthesis

The compounds of this disclosure may be prepared using any suitable synthetic scheme. The methodology used to prepare the compounds of this disclosure may involve two components. The first component may involve the formation of the chelator, while the second may involve the modification of the chelator by forming a reactive functional group, covalently attaching a conjugate, or covalently attaching a fluorophore moiety to form the desired indicator compound. Although these synthetic components are typically performed in the order given, they may be carried out in any other suitable sequence. For example, a portion of the chelator may be derivatized with a fluorescent dye prior to formation of the complete chelator ring. The appropriate methods may be used to synthesize the desired compounds of this disclosure.

As the metal binding ability of the resulting chelators may be significantly influenced by the nature of the amine substituents, careful selection of the alkylating agent may be necessary to prepare a reporter for a particular target ion. Crown ethers and aza-crown ethers are typically selective for lithium, sodium and potassium ion. Where the chelator nitrogens are alkylated by methyl bromoacetate, the resulting bis-aza-crown ether is typically selective for lithium, sodium and potassium ions. Selection of alkylating agent that incorporates a precursor to a reactive functional group is useful for producing chemically reactive compounds of this disclosure, as well as acting as a useful intermediate for preparing conjugates, as described above.

The syntheses of chelating groups selective for different metal ions has been well described in the literature (U.S. Pat. Nos. 4,603,209; 4,849,362; 5,049,673; 5,134,232; 5,453,517; 5,459,276; 5,501,980; 5,516,911, each of which is incorporated by reference). These methods can be readily adapted to prepare chelator intermediates useful for the synthesis of the compounds of this disclosure.

Synthesis of conventional xanthene dyes such as fluoresceins, rhodamines and rhodols typically involves the condensation of two equivalents of resorcinol (for fluoresceins), aminophenol (for rhodamines) or a mixture of a resorcinol and an aminophenol (for rhodols) with a carbonyl-containing moiety such as a phthalic acid derivative or benzaldehyde derivatives. However, in the synthesis of the xanthene indicators of this disclosure, the desired resorcinol or aminophenol is condensed with a chelator intermediate that contains a carboxylic acid, anhydride or acyl halide bound directly to the chelating moiety. These synthetic methods are demonstrated in the following examples.

Alternatively, the fluorescent indicators of this disclosure can be prepared via the condensation of properly protected xanthones with a chelator anion, typically prepared from the corresponding chelator bromide or iodide. This organometallic chemistry is also well described in the literature (C. Chen, R. Yeh and D. S. Lawrence, J. Am. Chem. Soc. 2002, 124, 3840; U.S. Pat. No. 5,049,673); Y. Urano, M. Kamiya, K. Kanda, T. Ueno, K. Hirose and T. Nagano, J. Am. Chem. Soc. 2005, 127, 4888) and can be readily adapted to synthesize the compounds of this disclosure.

Post-condensation modifications of both the chelator and the fluorophore moiety are typically analogous to known methods of indicator modification. For example, the reduction of nitro substituents to amino groups, the conversion of carboxy substituents to cyano groups, and the preparation of esters of carboxylic acids, including acetoxymethyl esters. Additionally, a given salt or counterion of the indicators of this disclosure may be readily converted to other salts by treatment with ion-exchange resins, selective precipitation, and basification, as is well-known in the art.

Post-condensation modifications of xanthylium dyes are well known. For instance, the xanthenone portion of the dye can be halogenated by treatment with an appropriate halogenating agent, such as liquid bromine. Xanthenes containing unsaturated fused rings can be hydrogenated to the saturated derivatives.

The reduced and oxidized versions of the xanthene indicators are freely interconvertible by well-known oxidation or reduction reagents, including borohydrides, aluminum hydrides, hydrogen/catalyst, and dithionites. Care must be exercised to select an oxidation or reducing agent that is compatible with the chelator used. A variety of oxidizing agents mediate the oxidation of dihydroxanthenes, including molecular oxygen in the presence or absence of a catalyst, nitric oxide, peroxynitrite, dichromate, triphenylcarbenium and chloranil. The dihydroxanthenes may also be oxidized electrochemically, or by enzyme action, including the use of horseradish peroxidase in combination with peroxides or by nitric oxide.

The fluorescent pyrrole-based indicators of this disclosure can be prepared via the condensation of a properly constructed pyrrole with a chelator aldehyde, a carboxylic acid or acid derivative such acyl chloride. The synthesis of pyrrole fluorophores is well known in the literature (See U.S. Pat. Nos. 4,774,339; 5,248,782; 5,451,663; 6,962,992; 9,423,396; Japan Pat. No. 2013168424; India Pat No. 201811044076; Chinese Pat. No. 109503640). These reported methods can be adapted to prepare the pyrrole-based indicators of this disclosure as demonstrated in the synthetic examples.

Applications of the Fluorescent Indicators

The indicators disclosed herein possess particular utility for the detection and/or quantification of metal ions such as $Li^+$, $Na^+$ and $K^+$ in a sample of interest. Such indicators may be useful for measuring ions in extracellular spaces; in vesicles; in vascular tissue of plants and animals; biological fluids such as blood and urine; in fermentation media; in environmental samples such as water, soil, waste water and seawater; and in chemical reactors. Optical indicators for ions are important for qualitative and quantitative determination of ions, particularly in living cells. Fluorescent indicators for metal cations also permit the continuous or intermittent optical determination of these ions in living cells, and in solutions containing the ions.

In effecting such determination, the substance to be determined, or analyte, which contains the ion of interest is contacted with a fluorescent indicator as disclosed above.

Complexation of the metal ion in the chelator of the indicator results in a detectable change in the fluorescence properties of the indicator. Detection and optionally quantification of the detectable change permits the ion of interest to be detected and optionally quantified.

Upon binding the target ion in the chelating moiety of the indicator, the optical properties of the attached fluorophore are generally affected in a detectable way, and this change may be correlated with the presence of the ion according to a defined standard. Compounds having relatively long wavelength excitation and emission bands can be used with a variety of optical devices and require no specialized (quartz) optics, such as are required by indicators that are excited or that emit at shorter wavelengths. These indicators are suitable for use in fluorescence microscopy, flow cytometry, fluorescence microplate readers, or any other application that currently utilize fluorescent metal ion indicators.

This determination method may be based on the so-called "PET effect", or the transfer, induced by photons, of electrons (photoinduced electron transfer=PET) from the ionophoric moiety or ionophore, respectively, to the fluorophore moiety or fluorophore, respectively, which leads to a decrease in the (relative) fluorescence intensity and the fluorescence decay time of the fluorophore. Absorption and emission wavelengths, however, are not significantly affected in the process (J. R. Lakowicz in "Topics in Fluorescence Spectroscopy", Volume 4: Probe Design and Chemical Sensing; Plenum Press, New York & London (1994)).

By the binding of ions to the ionophore, the PET effect may be partly or completely inhibited, so that there is an increase in the fluorescence of the fluorophore moiety. Hence, the concentration or the activity of the ion to be determined can be deduced by measuring the change in fluorescence properties, i.e., fluorescence intensity and/or fluorescence decay time.

For most biological applications, it is useful that the indicators be effective in aqueous solutions. It is also beneficial if the indicator absorbs and emits light in the visible spectrum where biological materials typically have low intrinsic absorbance or fluorescence. Optical methods using fluorescence detection of metal ions permit measurement of the entire course of ion flux in a single cell as well as in groups of cells. The advantages of monitoring transport by fluorescence techniques include the high level of sensitivity of these methods, temporal resolution, modest demand for biological material, lack of radioactivity, and the ability to continuously monitor ion transport to obtain kinetic information (Eidelman, O. Cabantchik, Z. I. Biochim. Biophys. Acta, 1989, 988, 319-334). The general principle of monitoring transport by fluorescence is based on having compartment-dependent variations in fluorescence properties associated with translocation of compounds. These aza-crown ethers may, depending on their structure, exhibit selectivity for lithium, sodium, or potassium ions. Some fluorescent indicators selective for $Li^+$, $Na^+$ and $K^+$ in aqueous or organic solution have also been described, based on the chemical modification of crown ethers (U.S. Pat. Nos. 5,134,232; 5,405,975, each hereby incorporated by reference).

The desired indicator compound is generally prepared for use as a detection reagent by dissolving the indicator in solution at a concentration that is optimal for detection of the indicator at the expected concentration of the target ion. Modifications that are designed to enhance permeability of the indicator through the membranes of live cells, such as functionalization of carboxylic acid moieties using acetoxymethyl esters and acetates, may require the indicator to be pre-dissolved in an organic solvent such as dimethylsulfoxide (DMSO) before addition to a cell suspension, where the indicators may then readily enter the cells. Intracellular enzymes then cleave the esters, generating more polar acids and phenols which are then well-retained inside the cells. For applications where permeability of cell-membranes is required, the indicators of this disclosure are typically substituted by only one fluorophore.

The specific indicator used in a particular assay or experiment may be selected based on the desired affinity for the target ion as determined by the expected concentration range in the sample, the desired spectral properties, and the desired selectivity. Initially, the suitability of a material as an indicator of ion concentration is commonly tested by mixing a constant amount of the indicating reagent with a measured amount of the target ion under the expected experimental conditions.

Where the binding of an ion in the metal ion-binding moiety of the indicator results in a detectable change in spectral properties of the indicator compound, that indicator may be used for the detection and/or quantification of that ion (the target ion). Although the change in spectral properties may include for example a change in absorption intensity or wavelength, preferably the change in spectral properties is a detectable fluorescence response. Preferred indicators display a high selectivity, that is, they show a sufficient rejection of non-target ions. The interference of a non-target ion is tested by a comparable titration of the indicator with that ion. In one aspect of this disclosure, the target ions for the indicators of the present invention are $Li^+$, $Na^+$ and $K^+$.

A detectable fluorescence response, as used herein, is a change in a fluorescence property of the indicator that is capable of being perceived, either by direct visual observation or instrumentally, the presence or magnitude of which is a function of the presence and/or concentration of a target metal ion in the test sample. This change in a fluorescence property is typically a change in fluorescence quantum yield, fluorescence polarization, fluorescence lifetime, a shift in excitation or emission wavelength, among others, or a combination of one or more of such changes in fluorescence properties. The detectable change in a given spectral property is generally an increase or a decrease. However, spectral changes that result in an enhancement of fluorescence intensity and/or a shift in the wavelength of fluorescence emission or excitation may also be useful. The change in fluorescence on ion binding may be due to conformational or electronic changes in the indicator that may occur in either the excited or ground state of the fluorophore, due to changes in electron density at the ion binding site, due to quenching of fluorescence by the bound target metal ion, or due to any combination of these or other effects.

A typical indicator for a specific target ion is an indicator that exhibits at least a 2-fold change in net fluorescence emission intensity (either an increase or decrease), or at least a 1 nanosecond difference in fluorescence lifetime (either shorter or longer). In one aspect of this disclosure, the indicator exhibits a 5-fold or greater change in net fluorescence emission intensity, and/or a 100% change in fluorescence lifetime in the presence of the target ion. In an alternative aspect of this disclosure, the indicator exhibits a shift in excitation or emission wavelength of at least 10 nm (either to shorter or longer wavelength), more preferably exhibiting a wavelength shift of 25 nm or greater.

The spectral response of a selected indicator to a specific metal ion is a function of the characteristics of the indicator in the presence and absence of the target ion. For example, binding to a metal ion may alter the relative electron densities of the fluorophore and the metal binding site. Additionally, or in the alternative, some metal ions may quench fluorescence emission when in close proximity to a fluorophore (heavy atom quenching). In one embodiment of this disclosure, the indicator is essentially nonfluorescent or exhibits low fluorescence in target ion-free solution and exhibits an increase in fluorescence intensity or fluorescence lifetime (or both) upon target metal ion binding.

As the optical response of the indicating reagent is typically determined by changes in fluorescence, the threshold of detection of the target ion will be dependent upon the sensitivity of the equipment used for its detection.

If the optical response of the indicator will be determined using fluorescence measurements, the sample of interest is typically stained with indicator concentrations of $10^{-9}$ M to $10^{-3}$ M. The most useful range of analyte concentration includes about one log unit above and below the dissociation constant of the ion-indicator complex. This dissociation constant may be determined by titration of the indicator with known concentrations of the target ion, usually over the range of virtually zero concentration to approximately 500 mM of the target ion, depending on which ion is to be measured and which indicator is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects are readily determined, and can be taken into account when calibrating a selected indicator.

The indicator is typically combined with a sample in a way that will facilitate detection of the target ion concentration in the sample. The sample is generally a fluid or liquid suspension that is known or suspected to contain the target ion. Representative samples include intracellular fluids from cells such as in blood cells, cultured cells, muscle tissue, neurons and the like; extracellular fluids in areas immediately outside of cells; fluids in vesicles; fluids in vascular tissue of plants and animals; biological fluids such as blood, saliva, and urine; biological fermentation media; environmental samples such as water, soil, waste water and sea water; industrial samples such as pharmaceuticals, foodstuffs and beverages; and samples from chemical reactors. Detection and quantitation of the target ion in a sample can help characterize the identity of an unknown sample, or facilitate quality control of a sample of known origin.

In one embodiment of this disclosure, the sample includes cells, and the indicator is combined with the sample in such a way that the indicator is added within the sample cells. By selection of the appropriate chelating moiety, fluorophore, and the substituents thereon, indicators may be prepared that will selectively localize in a desired organelle, and provide measurements of the target ion in those organelles. Conjugates of the indicators of this disclosure with organelle-targeting peptides may be used to localize the indicator to the selected organelle, facilitating measurement of target ion presence or concentration within the organelle (as described in U.S. Pat. No. 5,773,227, hereby incorporated by reference). Alternatively, selection of a lipophilic fluorophore, or a fluorophore having predominantly lipophilic substituents may result in localization of the indicator in lipophilic environments in the cell, such as cell membranes. Selection of cationic indicators will typically result in localization of the indicator in mitochondria.

In one embodiment of this disclosure, the indicator compound of this disclosure optionally further includes a metal ion. In another embodiment, the compounds of this disclosure, in any of the embodiments described above, are associated, either covalently or noncovalently, with a surface such as a microfluidic chip, a silicon chip, a microscope slide, a microplate well, or another solid or semisolid matrix, and is combined with the sample of interest as it flows over the surface. In this embodiment, the detectable optical response may therefore be detected on the matrix surface itself, typically by use of instrumental detection. This embodiment of this disclosure may be particularly suited to high-throughput screening using automated methods.

The fluorescence response of the indicator to the target ion may be detected by various means that include without limitation measuring fluorescence changes with fluorometers, fluorescence microscopes, laser scanners, flow cytometers, and microfluidic devices, as well as by cameras and other imaging equipment. These measurements may be made remotely by incorporation of the fluorescent ion sensor as part of a fiber optic probe. The indicator may be covalently attached to the fiber optic probe material, typically glass or functionalized glass (e.g., aminopropyl glass) or the indicator may be attached to the fiber optic probe via an intermediate polymer, such as polyacrylamide. The indicator solution is alternatively incorporated non-covalently within a fiber optic probe, as long as there is a means whereby the target ion may come into contact with the indicator solution. More preferably, the aza-crown ether indicators of this disclosure are used with a fluorescence microplate reader that is equipped with an automated liquid handling system such as FLIPR, FLEXSTATION and FDSS.

In another aspect of this disclosure, the fluorescent ion indicators of this disclosure may be used in combination with one or more non-fluorescent dyes that are not substantially cell-permeable in order to reduce the background fluorescence analogous to the methods described in U.S. Pat. No. 6,420,183, hereby incorporated by reference. Non-fluorescent dyes and dye mixtures that have large water solubilities and minimal effects on the physiology of the cells are preferred for this application. More preferably are water-soluble azo dyes (such as trypan blue), which have been used in cell-based assays for many years (H. W. Davis, R. W. Sauter. Histochemistry, 1977, 54, 177; W. E. Hathaway, L. A. Newby, J. H. Githens, Blood, 1964, 23, 517; C. W. Adams, O. B. Bayliss, R. S. Morgan, Atherosclerosis, 1977, 27, 353).

The screening methods described herein can be performed with cells growing in or deposited on solid surfaces. A common technique is to use a microwell plate where the fluorescence measurements are performing using a commercially available fluorescent plate reader. These methods lend themselves to use in high throughput screening using both automated and semi-automated systems.

Using the indicators of the present invention, the measurement of fluorescence intensity can provide a sensitive method for monitoring changes in intracellular ion concentrations. Thus, fluorescence measurements at appropriate excitation and emission wavelengths provide a fluorescence readout which is sensitive to the changes in the ion concentrations.

In one embodiment, a method of this disclosure includes a) adding a compound as described above to a sample containing a cell; b) incubating the sample for a time sufficient for the compound to be loaded into the cell and an indicator compound to be generated intracellularly; c) illuminating the sample at a wavelength that generates a fluorescence response from the indicator compound; d) detecting a fluorescence response from the indicator compound; and e) correlating the fluorescence response with the presence of intracellular calcium.

In one aspect of this disclosure, the disclosed method is useful for screening potential therapeutic drugs, for example drugs which may affect ion concentrations in biological cells. These methods may include measuring ion concentrations as described above in the presence and absence (as a control measurement) of the test sample. Control measurements are usually performed with a sample containing all components of the test sample except for the putative drug being screened. Detection of a change in ion concentration in the presence of the test agent relative to the control indicates that the test agent is active. Ion concentrations can also be determined in the presence or absence of a pharmacologic agent of known activity (i.e., a standard agent) or putative activity (i.e., a test agent). A difference in ion concentration as detected by the methods disclosed herein allows one to compare the activity of the test agent to that of a standard agent of known activity. It will be recognized that many combinations and permutations of drug screening protocols are known to one of skill in the art and they may be readily adapted to use with the method of ion concentration measurement disclosed herein to identify compounds which affect ion concentrations.

In one aspect of this disclosure, the disclosed indicators have the minimal assay background in their masked form since their non-hydrolyzed esters cannot be excited at 488 nm, the common excitation wavelength equipped with almost all the fluorescence instruments.

In yet another aspect of this disclosure, the fluorescent ion indicators are used in a method to measure lithium ion concentrations. Compound 15 is dissolved in Tris-HCl (pH 7.0) to make a dye stock solution. The equal amount of Compound 15 is added to a variety of LiCl solutions with all the solutions having 2.5 μM Compound 15 and LiCl concentrations varied from 0, 0.62, 1.85, 5.56, 16.67, 50, 150, 450 mM (from bottom to top). The fluorescence intensities measured and recorded for all the solutions under the same conditions as demonstrated in FIG. 10.

In yet another aspect of this disclosure, the disclosed method may facilitate the screening of test samples in order to identify one or more compounds that are capable of modulating the activity of an ion channel, pump or exchanger in a membrane, and the method further includes stimulating the cell, monitoring changes in the intensity of the fluorescence response from the indicator compound, and correlating the changes in fluorescence intensity with changes in intracellular calcium levels.

An additional method may be used to evaluate the efficacy of a stimulus that generates a target ion response, including (a) loading a first set and a second set of cells with the ion indicators of this disclosure which monitor ion concentrations; (b) optionally, exposing both the first and second set of cells to a stimulus which modulates the ion channel, pump or exchanger; (c) exposing the first set of cells to the test sample; (d) measuring the ion concentrations in the first and second sets of cells; and (e) relating the difference in ion concentrations between the first and second sets of cells to the ability of a compound in the test sample to modulate the activity of an ion channel, pump or exchanger in cells. In one aspect of the recited method, the method may include the addition of probenecid or a probenecid derivative to the sample.

One or more of the methods disclosed herein may be enhanced by the addition of a cell-impermeant and non-fluorescent dye to the sample, such that the dye remains in the extracellular solution, and acts as an acceptor dye for energy transfer from the indicator compound, thereby decreasing background signal from the sample solution. In one aspect of the method, the cell-impermeant and non-fluorescent dye is a water-soluble azo dye.

Ion channels of particular interest may include, but are not limited to, sodium, calcium, potassium, nonspecific cation, and chloride ion channels, each of which may be constitutively open, voltage-gated, ligand-gated, or controlled by intracellular signaling pathways.

Biological cells of potential interest for screening application may include, but are not limited to, primary cultures of mammalian cells, cells dissociated from mammalian tissue, either immediately or after primary culture. Cell types may include, but are not limited to white blood cells (e.g., leukocytes), hepatocytes, pancreatic beta-cells, neurons, smooth muscle cells, intestinal epithelial cells, cardiac myocytes, glial cells, and the like. The disclosed method may also include the use of recombinant cells into which ion transporters, ion channels, pumps and exchangers have been inserted and expressed by genetic engineering. Many cDNA sequences for such transporters have been cloned (see U.S. Pat. No. 5,380,836 for a cloned sodium channel, hereby incorporated by reference) and methods for their expression in cell lines of interest are within the knowledge of one of skill in the art (see, U.S. Pat. No. 5,436,128, hereby incorporated by reference). Representative cultured cell lines derived from humans and other mammals include LM cells, HEK-293 (human embryonic kidney cells), 3T3 fibroblasts, COS cells, CHO cells, RAT1 and HepG2 cells, Hela cells, $U_2OS$ cells and Jurkat cells etc.

Assay Kits

Due to the advantageous properties and the simplicity of use of the disclosed ion indicator compounds, they possess particular utility in the formulation of a kit for the complexation, detection, or quantification of selected target ions. An exemplary kit may include one or more compounds or compositions of this disclosure in any of the embodiments described above, either present as a pure compound, in a suitable composition, or dissolved in an appropriate stock solution. The kit may further include instructions for the use of the indicator compound to complex or detect a desired target ion. The kit may further include one or more additional components, such as an additional detection reagent.

The indicator of this disclosure may be present in the kit associated with a surface, such as a chip, microplate well, or other solid or semi-solid matrix.

The additional kit components may be selected from, without limitation, calibration standards of a target ion, ionophores, fluorescence standards, aqueous buffers, surfactants and organic solvents. The additional kit components may be present as pure compositions, or as aqueous solutions that incorporate one or more additional kit components. Any or all of the kit components optionally further comprise buffers.

In one aspect of the disclosed kit, the kit includes at least one indicator compound as described above, and a non-fluorescent and cell-impermeant quencher dye. The non-fluorescent and cell-impermeant quencher dye is optionally present in a combined buffer solution with the compound, or the buffer solution of the cell-impermeant quencher dye is present in a separate container from the indicator compound.

The examples provided below illustrate selected aspects of the invention. They are not intended to limit or define the entire scope of the invention.

EXAMPLES

Example 1. The Preparation of Compound 1

1

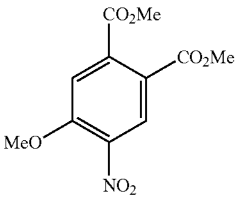

Dimethyl 4-hydroxy-5-nitrophthalate (5 g) is dissolved in DMF (30 mL). To the DMF solution $K_2CO_3$ (6.42 g) and methyl iodide (6.7 mL) are added. The mixture is stirred at RT overnight. DMF is removed by a rotavapor under high vacuum. EtOAc and water are added, the aqueous solution is extracted with EtOAc. The EtOAc solution is washed with water and brine, dried over anhydrous $Na_2SO_4$. The solution is filtered, concentrated and dried to give Compound 1.

Example 2. The Preparation of Compound 2

2

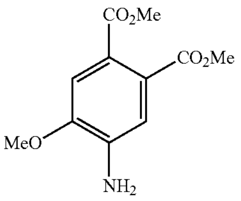

Compound 2 (5.0 g) is dissolved in DMF (80 mL). To the DMF solution, 10% Pd on carbon powder (1.0 g) is added. The mixture is subjected to hydrogenation for 2 days. The 10% Pd on carbon powder is filtered through a celite pad and washed with MeOH. The solvents are removed to give crude Compound 2.

Example 3. The Preparation of Compound 3

3

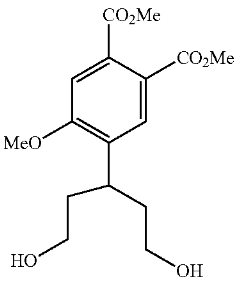

Compound 2 (1.73 g) is dissolved in MeCN (50 mL). To the MeCN solution, 2-bromoethanol (15 mL), DIEA (15 mL) and NaI (0.5 g) are added. The mixture is refluxed for 2 weeks. MeCN and DIEA are removed by a rotavapor. The residue is dissolved in EtOAc (200 mL) and then washed with brine. The organic phase is separated, and dried over anhydrous $Na_2SO_4$, filtered and concentrated to give a crude oil. The crude oil is dissolved in $CH_2C_2$ and purified on a silica gel column using a gradient of EtOAc/MeOH as an eluant to give Compound 3.

Example 4. The Preparation of Compound 4

4

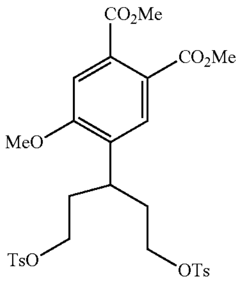

Compound 3 (400 mg) is dissolved in dry $CH_2Cl_2$ (10 mL), and to the $CH_2Cl_2$ solution p-TsCl (590 mg) and $NEt_3$ (0.5 mL) are added. The reaction mixture is stirred at RT for 6 h. The solution is concentrated, and the resulted residue is dissolved in EtOAc. The solution is washed with 0.5 N HCl/water and brine respectively, dried over anhydrous $Na_2SO_4$. The solution is filtered, concentrated and dried to give crude oil. The oil is dissolved in $CH_2Cl_2$ and purified on a silica gel column using a gradient of EtOAc/hexanes as eluants to give compound 4.

Example 5. The Preparation of Compound 5

5

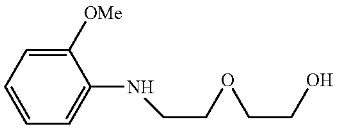

2-Methoxyaniline (9.3 g) and 2-(2-chloroethoxy)ethanol (6.5 g) are dissolved in MeCN (150 mL), and to the MeCN solution DIEA (13 mL) and NaI (3.0 g) are added. The mixture is refluxed for 3 days. Most MeCN is removed, EtOAc and water are added. The aqueous solution is extracted with EtOAc. The EtOAc layer is washed with water and then brine, dried over anhydrous $Na_2SO_4$. The solution is filtered, concentrated and dried to give a crude oil. The oil is dissolved in $CH_2Cl_2$ and purified on a silica gel column using a gradient of EtOAc/$CH_2Cl_2$ as eluants to give Compound 5.

Example 6. The Preparation of Compound 6

6

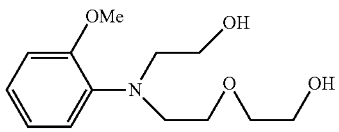

Compound 5 (10.6 g) is dissolved in MeCN (120 mL), to the MeCN solution 2-bromoethanol (6.6 mL), DIEA (13 mL) and NaI (1.0 g) are added. The mixture is refluxed for 3 days. Most MeCN is removed, and water is added. The aqueous solution is adjusted pH to 1-2 with 20% TFA/water and purified on a C18 column using 0.1% TFA/water and MeCN as solvents. The pure fractions are combined, neutralized with saturated $NaHCO_3$ aqueous solution and concentrated to give compound 6.

Example 7. The Preparation of Compound 7

7

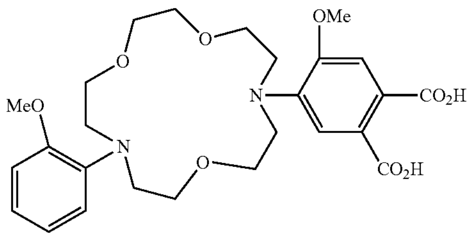

Compound 6 (120 mg) is dissolved in dry THF (5 mL) and then NaH (60 mg) is added. The mixture is stirred at RT for 30 min and mixed with Compound 4 (300 mg) in dry THF (5 mL). The mixture is stirred at RT for 2 days, and then water (10 mL) is added. The reaction mixture is adjusted pH>12 with 1N NaOH/water, stirred at RT for 2 h, and then adjusted pH to 7-8 with 1 N HCl/water. THF is removed under high vacuum, and the mixture is centrifuged to remove precipitate. The aqueous solution is further purified by HPLC using 0.1% TFA/water and MeCN as solvents to give compound 7.

Example 8. The Preparation of Compounds 8 and 9

8

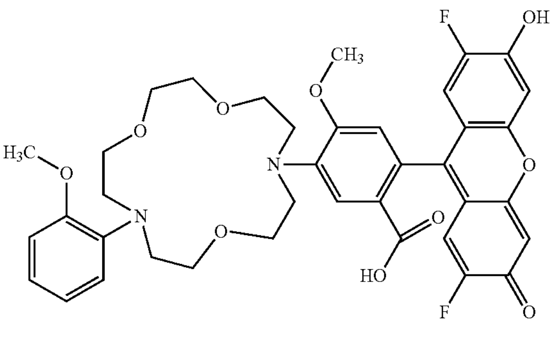

-continued

9

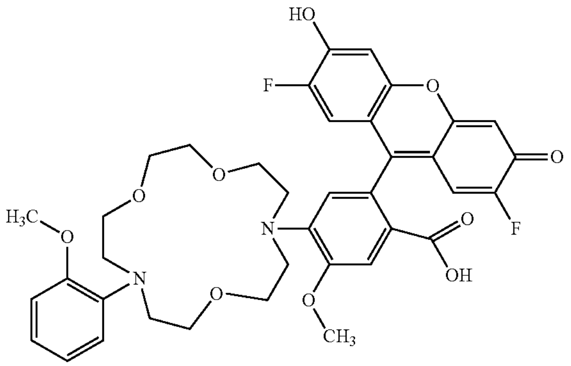

Compound 7 (30 mg) is dissolved in $Ac_2O$ (2 mL) and the resulted mixture is stirred at 95° C. for 5 min. $Ac_2O$ is removed and dried under vacuum. $MeSO_3H$ (2 mL) and 4-fluororesorcinol (20 mg) are added. The mixture is stirred at 95° C. for 7 h, and then poured into ice/water. The mixture is adjusted pH to 7-8 with $NEt_3$ and TEAB buffer, purified by HPLC using TEAB buffer and MeCN as solvents to give Compounds 8 and 9 respectively.

Example 9. The Preparation of Compound 10

10

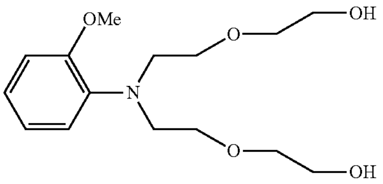

2-Methoxyaniline (5.7 g) is dissolved in MeCN (100 mL), to the MeCN solution 2-(2-chloroethoxy)ethanol (20.0 g), DIEA (24 mL) and NaI (3.0 g) are added. The mixture is refluxed for 4 days. Most MeCN is removed, and water is added. The aqueous solution is adjusted pH to 1-2 with 20% TFA/water, and then purified on a C18 column using 0.1% TFA/water and MeCN as solvents. The pure fractions are combined, neutralized with saturated $NaHCO_3$ aqueous solution, concentrated to give compound 10.

Example 10. The Preparation of Compound 11

11

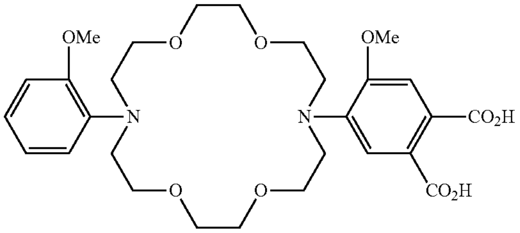

Compound 10 (110 mg) is dissolved in dry THF (10 mL) and then KH (150 mg, 30% in oil) is added. The mixture is stirred at RT for 30 min and mixed with Compound 4 (200 mg) in dry THF (5 mL). The mixture is stirred at RT for 2 days, and then water (10 mL) is added. The reaction mixture is adjusted pH>12 with 1 N NaOH/water, stirred at RT for 2 h, and then adjusted pH to 7-8 with 1 N HCl/water. THF is removed under high vacuum, and the mixture is centrifuged to remove precipitate. The aqueous solution is further purified by HPLC using 0.1% TFA/water and MeCN as solvents to give compound 11.

Example 11. The Preparation of Compounds 12 and 13

12

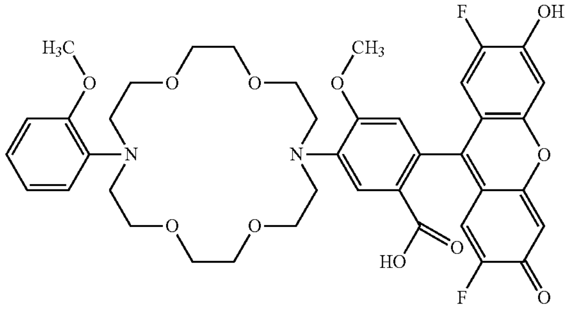

13

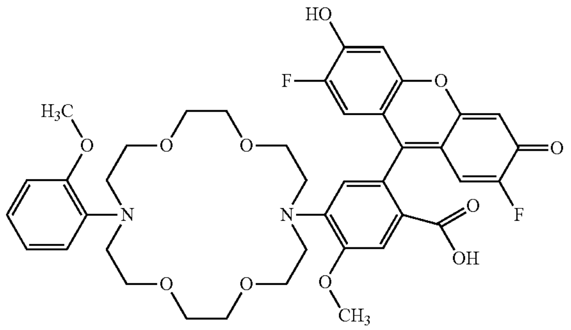

Compound 11 (20 mg) is dissolved in $Ac_2O$ (2 mL) and the resulted mixture is stirred at 95° C. for 5 min. $Ac_2O$ is removed and dried under vacuum. $MeSO_3H$ (2 mL) and 4-fluororesorcinol (20 mg) are added. The mixture is stirred at 95° C. for 7 h, and then poured into water. The mixture is adjusted pH to 7-8 with $NEt_3$ and TEAB buffer, purified by HPLC using TEAB buffer and MeCN as solvents to give Compounds 12 and 13 respectively.

Example 12. The Preparation of Compound 14

14

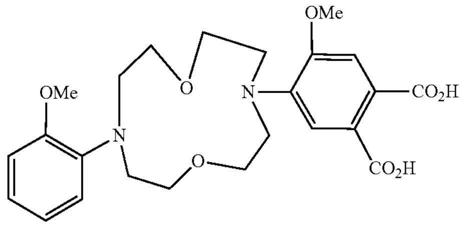

Compound 12 is prepared analogously from the reaction of Compound 4 with 2'-((2-methoxyphenyl)azanediyl)bis(ethan-1-ol) as described in Example 10.

Example 13. The Preparation of Compounds 15 and 16

15

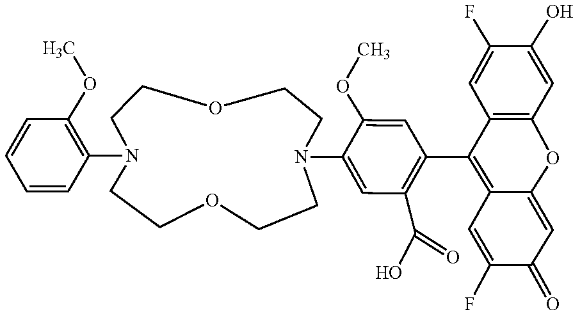

16

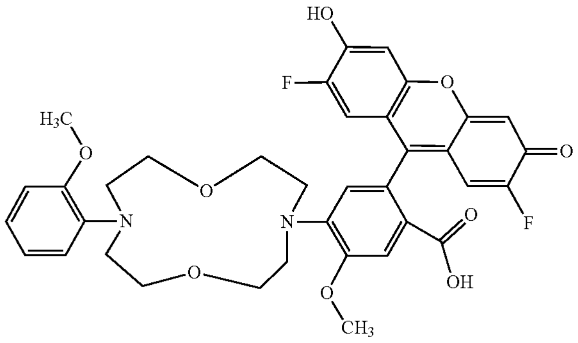

Compounds 15 and 16 are prepared analogously from the reaction of Compound 14 with 4-fluororesorcinol as described in Example 11.

Example 14. The Preparation of Compound 17

17

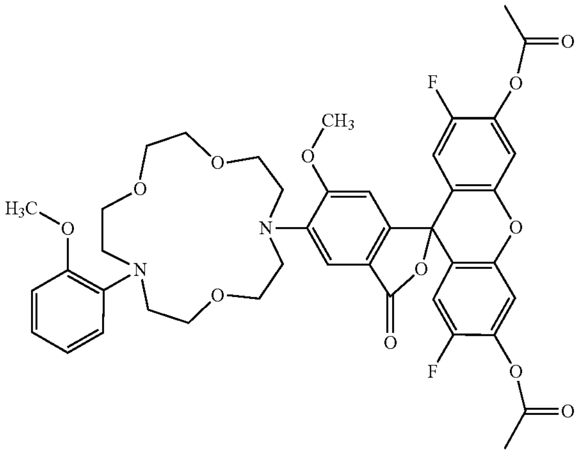

Compound 12 (5 mg) is dissolved in pyridine (1 mL) and to the pyridine solution is added $Ac_2O$ (0.1 mL). The reaction mixture is stirred at RT for 30 min and concentrated under high vacuum. EtOAc and water are added, the aqueous solution is extracted with EtOAc. The EtOAc extract is washed with water, concentrated, and dried to give the crude Compound 14 that is further purified on a silica gel column using a gradient of $EtOAc/CH_2Cl_2$ as eluants to give the Compound 17.

Example 15. The Preparation of Compound 19

19

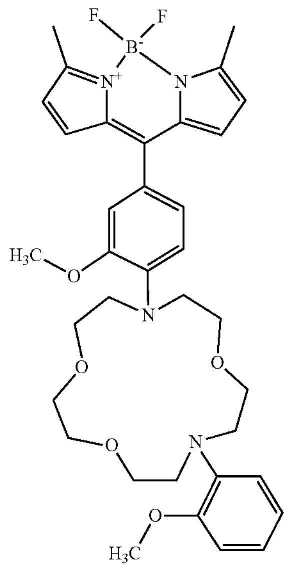

Compound 19 is prepared from 3-methoxy-4-(13-(2-methoxyphenyl)-1,4,10-trioxa-7,13-diazacyclopentadecan-7-yl)benzaldehyde and 2-methylpyrrole as analogously to the procedure described by V. Martin et al (U.S. Pat. No. 6,962,992).

The other useful indicators (e.g., listed in the following Table 1) can be analogously prepared as described in the above examples.

TABLE 1

Other exemplary indicators

| Compound | Structure |
|---|---|
| 20 | 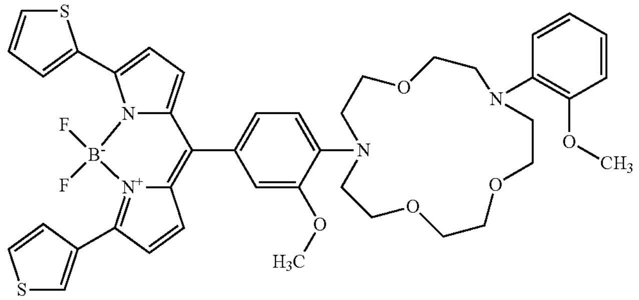 [SMILES: COc1ccccc1N1CCOCCOCCN(c2ccc(C3=C4C=CC(c5ccsc5)=[N+]4[B-](F)(F)n4c3ccc4-c3cccs3)cc2OC)CCOCC1] |
| 21 | 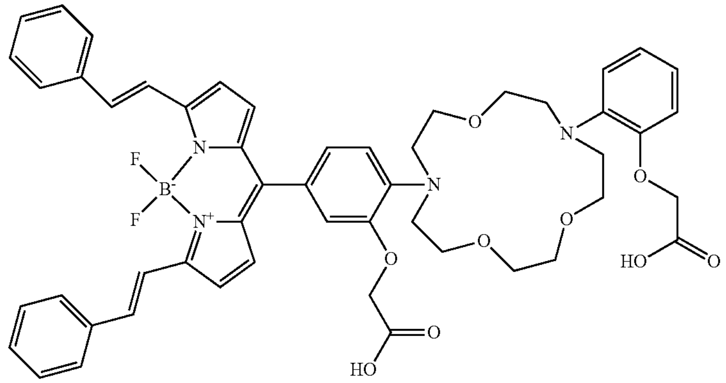 [SMILES: O=C(O)COc1ccccc1N1CCOCCOCCN(c2ccc(C3=C4C=CC(/C=C/c5ccccc5)=[N+]4[B-](F)(F)n4c(/C=C/c5ccccc5)ccc43)cc2OCC(=O)O)CCOCC1] |

TABLE 1-continued
| Other exemplary indicators | |
|---|---|
| Compound | Structure |
| 22 | 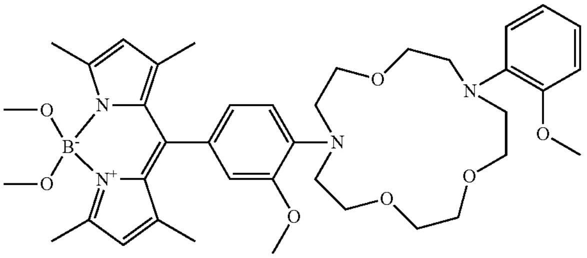 |
| 23 | 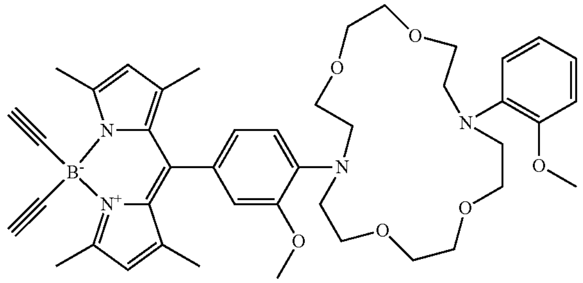 [SMILES: C#C[B-]1(C#C)n2c(C)cc(C)c2C(c2ccc(N3CCOCCOCCN(c4ccccc4OC)CCOCCOCC3)c(OC)c2)=C2C(C)=CC(C)=[N+]21] |
| 24 | 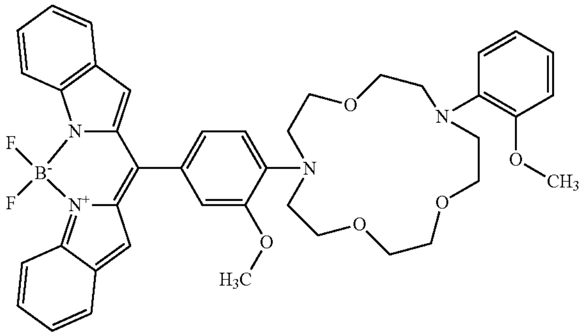 [SMILES: COc1ccccc1N1CCOCCOCCN(c2ccc(C3=C4C=c5ccccc5=[N+]4[B-](F)(F)n4c3cc3ccccc34)cc2OC)CCOCC1] |
| 25 | 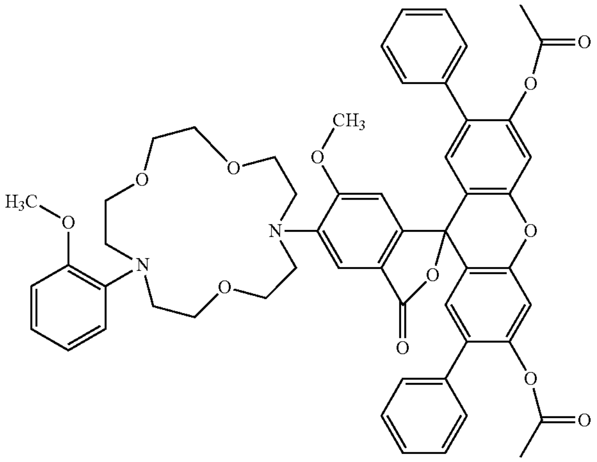 [SMILES: COc1ccccc1N1CCOCCOCCN(c2cc3c(cc2OC)C2(OC3=O)c3cc(-c4ccccc4)c(OC(C)=O)cc3Oc3cc(OC(C)=O)c(-c4ccccc4)cc32)CCOCC1] |

TABLE 1-continued
| Other exemplary indicators | |
|---|---|
| Compound | Structure |
| 26 | 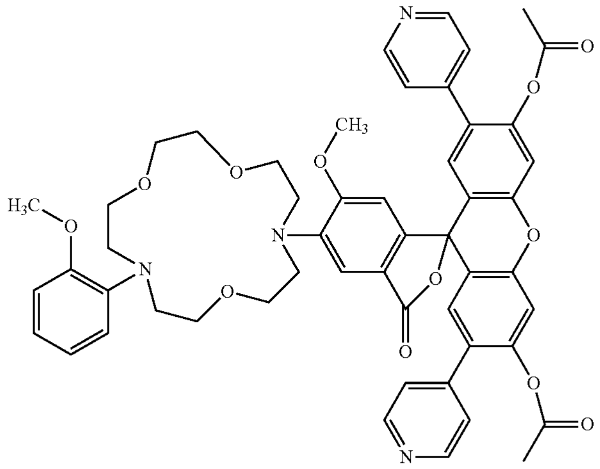 [SMILES: COc1ccccc1N1CCOCCOCCN(c2cc3c(cc2OC)C2(OC3=O)c3cc(-c4ccncc4)c(OC(C)=O)cc3Oc3cc(OC(C)=O)c(-c4ccncc4)cc32)CCOCC1] |
| 27 | 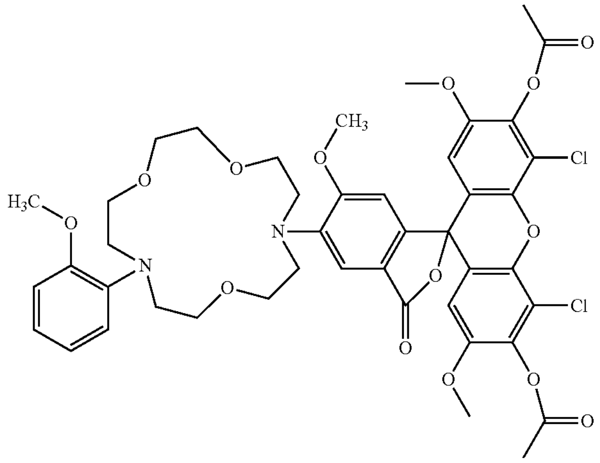 [SMILES: COc1ccccc1N1CCOCCOCCN(c2cc3c(cc2OC)C2(OC3=O)c3cc(OC)c(OC(C)=O)c(Cl)c3Oc3c2cc(OC)c(OC(C)=O)c3Cl)CCOCC1] |
| 28 | 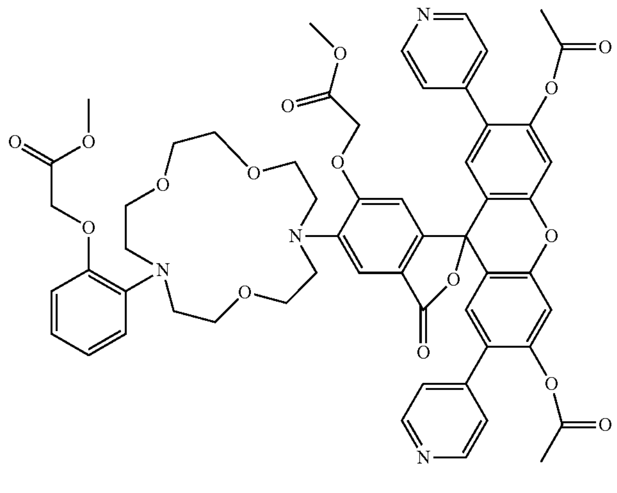 [SMILES: COC(=O)COc1ccccc1N1CCOCCOCCN(c2cc3c(cc2OCC(=O)OC)C2(OC3=O)c3cc(-c4ccncc4)c(OC(C)=O)cc3Oc3cc(OC(C)=O)c(-c4ccncc4)cc32)CCOCC1] |

TABLE 1-continued
| Other exemplary indicators | |
|---|---|
| Compound | Structure |
| 29 | 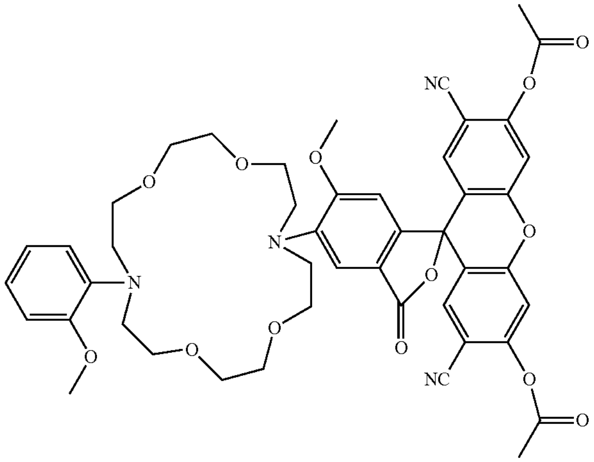 [SMILES: COc1ccccc1N1CCOCCOCCN(c2cc3c(cc2OC)C2(OC3=O)c3cc(C#N)c(OC(C)=O)cc3Oc3cc(OC(C)=O)c(C#N)cc32)CCOCCOCC1] |
| 30 | 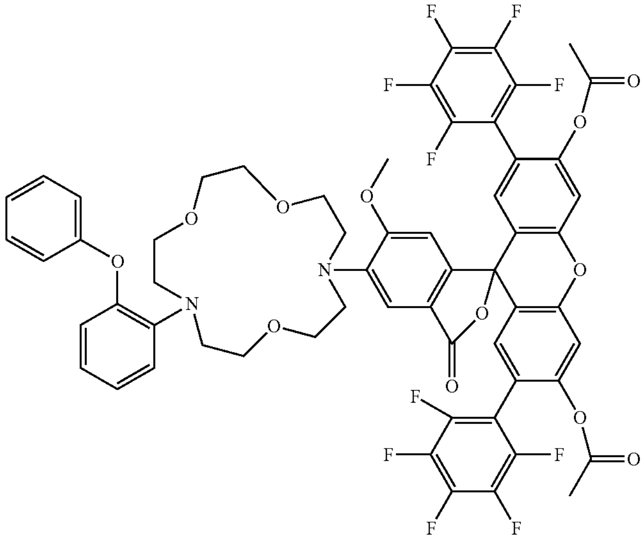 [SMILES: COc1cc2c(cc1N1CCOCCOCCN(c3ccccc3Oc3ccccc3)CCOCC1)C(=O)OC21c2cc(-c3c(F)c(F)c(F)c(F)c3F)c(OC(C)=O)cc2Oc2cc(OC(C)=O)c(-c3c(F)c(F)c(F)c(F)c3F)cc21] |
| 31 | 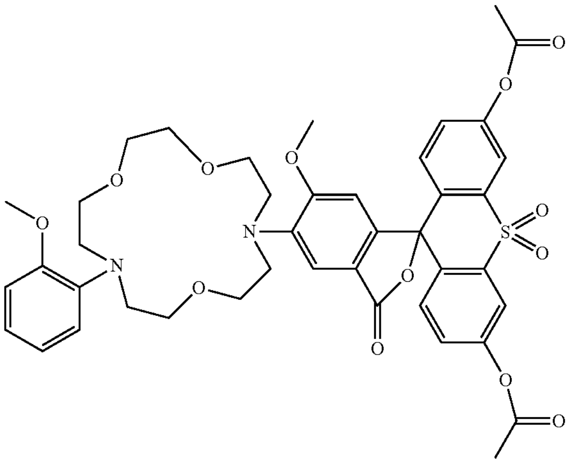 [SMILES: COc1ccccc1N1CCOCCOCCN(c2cc3c(cc2OC)C2(OC3=O)c3ccc(OC(C)=O)cc3S(=O)(=O)c3cc(OC(C)=O)ccc32)CCOCC1] |

TABLE 1-continued
| Other exemplary indicators | |
|---|---|
| Compound | Structure |
| 32 | 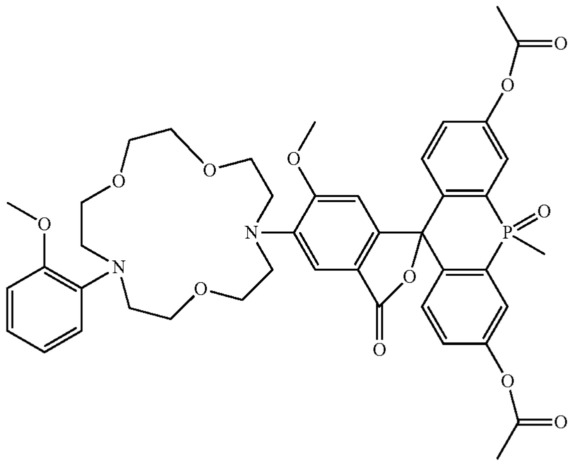 [SMILES: COc1ccccc1N1CCOCCOCCN(c2cc3c(cc2OC)C2(OC3=O)c3ccc(OC(C)=O)cc3P(C)(=O)c3cc(OC(C)=O)ccc32)CCOCC1] |
| 33 | 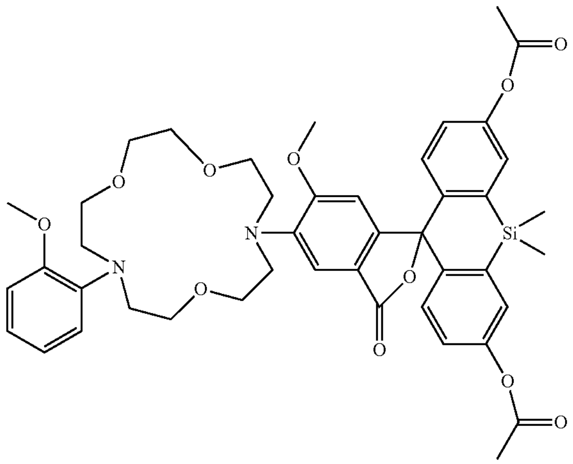 [SMILES: COc1ccccc1N1CCOCCOCCN(c2cc3c(cc2OC)C2(OC3=O)c3ccc(OC(C)=O)cc3[Si](C)(C)c3cc(OC(C)=O)ccc32)CCOCC1] |
| 34 | 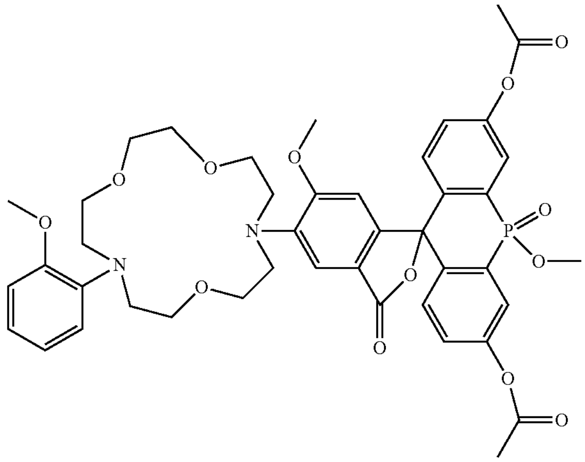 [SMILES: COc1ccccc1N1CCOCCOCCN(c2cc3c(cc2OC)C2(OC3=O)c3ccc(OC(C)=O)cc3P(=O)(OC)c3cc(OC(C)=O)ccc32)CCOCC1] |

TABLE 1-continued
| Other exemplary indicators | |
|---|---|
| Compound | Structure |
| 35 | 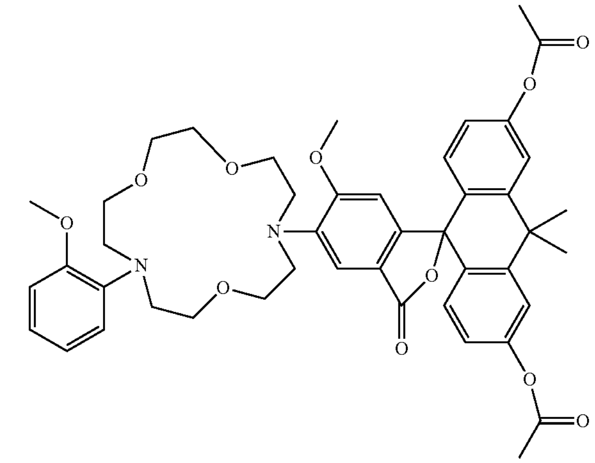 [SMILES: COc1ccccc1N1CCOCCOCCN(c2cc3c(cc2OC)C2(OC3=O)c3ccc(OC(C)=O)cc3C(C)(C)c3cc(OC(C)=O)ccc32)CCOCC1] |
| 36 | 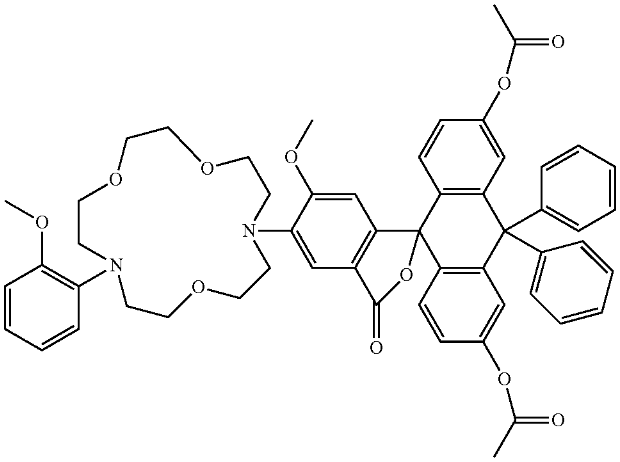 [SMILES: COc1ccccc1N1CCOCCOCCN(c2cc3c(cc2OC)C2(OC3=O)c3ccc(OC(C)=O)cc3C(c3ccccc3)(c3ccccc3)c3cc(OC(C)=O)ccc32)CCOCC1] |
| 37 | 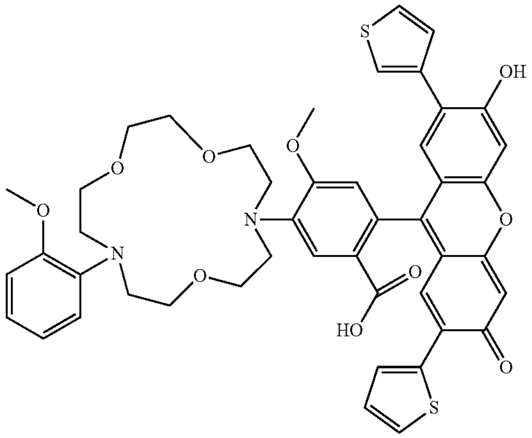 [SMILES: COc1ccccc1N1CCOCCOCCN(c2cc(C(=O)O)c(-c3c4cc(-c5cccs5)c(=O)cc-4oc4cc(O)c(-c5ccsc5)cc34)cc2OC)CCOCC1] |

TABLE 1-continued
| Other exemplary indicators | |
|---|---|
| Compound | Structure |
| 38 | 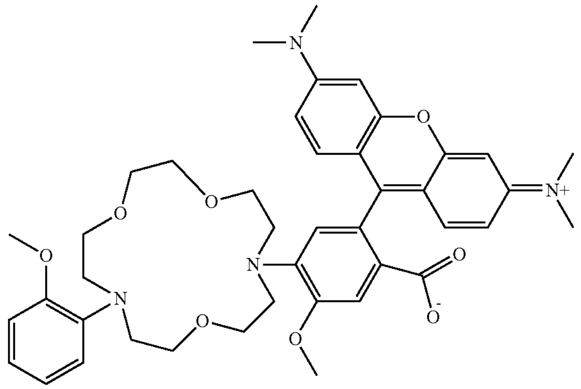 [SMILES: COc1ccccc1N1CCOCCOCCN(c2cc(-c3c4ccc(=[N+](C)C)cc-4oc4cc(N(C)C)ccc34)c(C(=O)O)cc2OC)CCOCC1] |
| 39 | 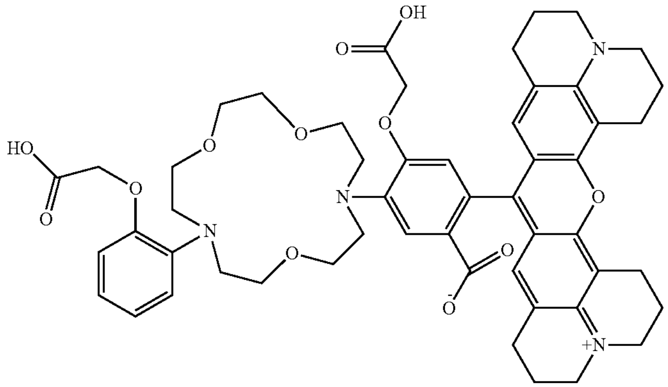 [SMILES: O=C(O)COc1ccccc1N1CCOCCOCCN(c2cc(C(=O)O)c(C3=c4cc5c6c(c4Oc4c3cc3c7c4CCCN7CCC3)CCC[N+]=6CCC5)cc2OCC(=O)O)CCOCC1] |
| 40 | 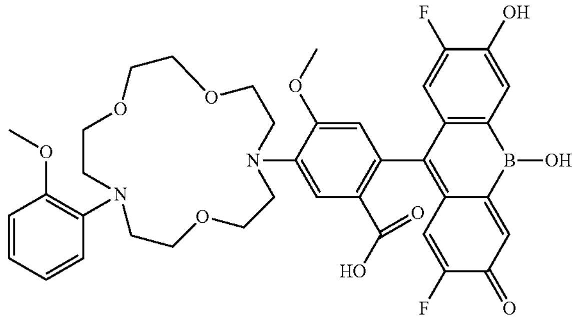 [SMILES: COc1ccccc1N1CCOCCOCCN(c2cc(C(=O)O)c(C3=C4C=C(F)C(=O)C=C4B(O)c4cc(O)c(F)cc43)cc2OC)CCOCC1] |
| 41 | 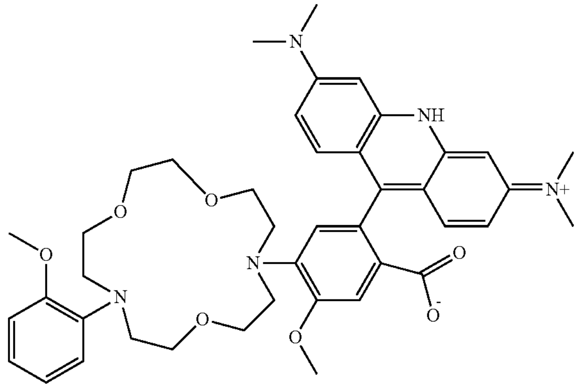 [SMILES: COc1ccccc1N1CCOCCOCCN(c2cc(-c3c4ccc(=[N+](C)C)cc-4[nH]c4cc(N(C)C)ccc34)c(C(=O)O)cc2OC)CCOCC1] |

TABLE 1-continued

| Other exemplary indicators | |
|---|---|
| Compound | Structure |
| 42 | 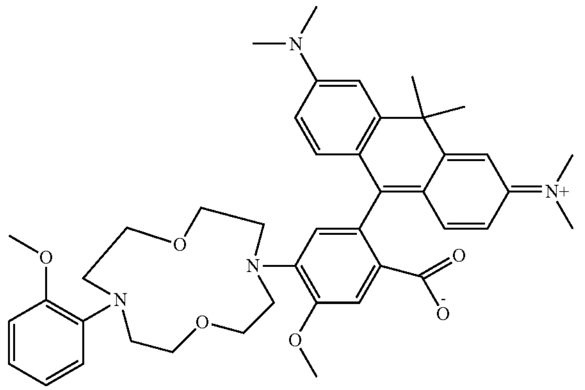 [SMILES: COc1ccccc1N1CCOCCN(c2cc(C3=C4C=CC(=[N+](C)C)C=C4C(C)(C)c4cc(N(C)C)ccc43)c(C(=O)O)cc2OC)CCOCC1] |
| 43 | 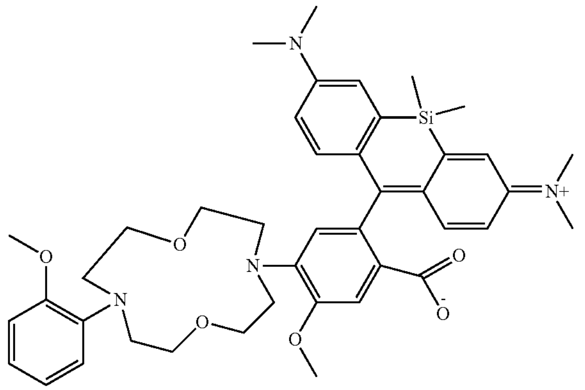 [SMILES: COc1ccccc1N1CCOCCN(c2cc(C3=C4C=CC(=[N+](C)C)C=C4[Si](C)(C)c4cc(N(C)C)ccc43)c(C(=O)O)cc2OC)CCOCC1] |

Example 16. Intracellular Ion Responses of the Fluorescent Indicators

The fluorescent compounds of this disclosure are useful for any application where it is desirable to complex a target metal ion. In order for a particular indicator of the present invention to be useful for intracellular detection purposes, it must exhibit a detectable change in spectral properties upon complexation of the desired metal ion (target ion) in cells. A typical method for binding target metal ions in a cell sample comprises the following steps: a) contacting cells with a fluorescent lipophilic compound of the present invention; and, b) incubating the cells and the lipophilic fluorescent indicator compound for sufficient time to allow the indicator compound to release its polar chelate to form a complex with a target metal ion whereby the metal ion is bound. The cell sample is illuminated with an appropriate wavelength whereby the target ion is detected. In such an assay the target ion can also be quantitated and monitored. As demonstrated in FIG. 9, HeLa cells are plated overnight in growth medium (DMEM). On the next day, growth medium is removed, and cells are washed with PBS. Compound 17 is dissolved in HHBS buffer containing 0.02% PF-127 to make a 10 μM dye working solution. 200 μL of the dye working solution is added. Cells are incubated at 37° C. and incubated for 30 minutes. The dye working solution is removed and HHBS buffer is added. The fluorescence images are acquired with Keyence BZ-X710 fluorescence microscope with FITC filter set.

The specific indicator used in an assay or experiment is selected based on the desired affinity for the target ion as determined by the expected concentration range in the sample, the desired spectral properties, desired cell permeability and the desired selectivity. Initially, the suitability of a material as an indicator of ion concentration is commonly tested by mixing a constant amount of the indicating reagent with a measured amount of the target ion under the expected experimental conditions. Preferred indicators display a high selectivity, that is, they show a sufficient rejection of non-target ions. The interference of a non-target ion is tested by a comparable titration of the indicator with that ion. Although preferred target ions for most indicators of the present invention are $Li^+$, $Na^+$ and $K^+$, any ion that yields a detectable change in absorption wavelengths, emission wavelengths, fluorescence lifetimes or other measurable optical property over the concentration range of interest is potentially measured using one of the indicators of this invention.

Modifications to the electronic structure of the fluorescent indicator to produce an indicator having the appropriate combination of binding affinity, ion selectivity and spectral response for a wide variety of metal ions. The indicator is generally prepared for use as a detection reagent by dissolving the indicator in solution at a concentration that is optimal for detection of the indicator at the expected concentration of the target ion.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

What is claimed is:

1. A compound of Formula 1:

Formula 1

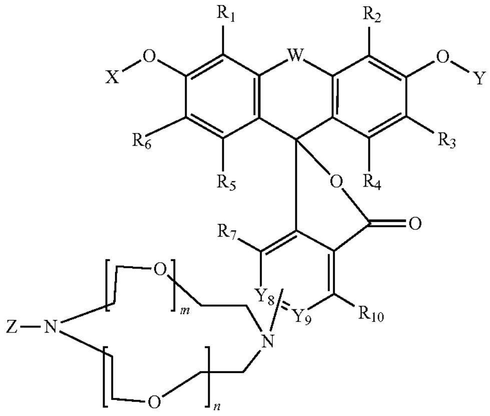

or a salt thereof, wherein:

$Y_8$ is $CR_8$ or C covalently bonded to N, and $Y_9$ is $CR_9$ or C covalently bonded to N, wherein one of $Y_8$ and $Y_9$ is C covalently bonded to the N;

$R_1$ to $R_{10}$ are independently selected from H, halogen, carboxy, substituted carboxy, alkyl, substituted alkyl, alkoxy, substituted alkoxy, aryloxy, substituted aryloxy, thiol, alkylthiol, arylthiol, azido, nitro, nitroso, cyano, amino, substituted amino, hydroxy, phosphonyl, sulfonyl, carbonyl, boronic acid, aryl, substituted aryl, heteroaryl, and substituted heteroaryl;

m and n are independently an integer from 0 to 3, wherein the sum of m+n is ≥2;

W is O, N—$R_{31}$, $C(R_{31}R_{32})$, $Si(R_{31}R_{32})$, S═O, O═S═O, P═$R_{32}$, O═P—$R_{32}$, O═P—$OR_{32}$, or $B(OR_{31})$, wherein $R_{31}$ and $R_{32}$ are independently selected from H, alkyl, substituted alkyl, aryl, substituted aryl, heteroaryl, and substituted heteroaryl;

X and Y are independently acyl, substituted acyl, acyloxymethyl or substituted acyloxymethyl; and Z is substituted aryl, wherein Z is substituted at the alpha position with a heteroatom-containing substituent capable of bonding to a chelated metal ion.

2. The compound of claim 1, wherein:

$R_1$-$R_{10}$ are independently H, halogen, carboxy, substituted carboxy, alkoxy, aryloxy, thiol, alkylthiol, arylthiol, azido, nitro, nitroso, cyano, amino, hydroxy, phosphonyl, sulfonyl, carbonyl, boronic acid, optionally substituted aryl, optionally substituted heteroaryl, optionally substituted alkyl, or optionally substituted alkoxy, wherein substituted aryl, substituted heteroaryl, substituted alkyl, and substituted alkoxy are substituted with one or more substituents selected from halogen, amino, hydroxy, phosphonyl, sulfonyl, carbonyl, boronic acid, aryl, and heteroaryl.

3. The compound of claim 1, wherein one of $R_8$ and $R_9$ is a heteroatom-containing substituent capable of bonding to a chelated metal ion.

4. The compound of claim 1, wherein:

i) $Y_9$ is covalently bonded to the N, and $R_8$ is alkoxy or substituted alkoxy; or ii) $Y_8$ is covalently bonded to the N, and $R_9$ is alkoxy or substituted alkoxy; and wherein:

$R_1$, $R_2$, $R_4$, $R_5$, $R_7$ and $R_{10}$ are each H; and $R_3$ and $R_6$ are independently halogen, aryl, substituted aryl, heteroaryl, substituted heteroaryl, alkoxy, substituted alkoxy, or cyano.

5. The compound of claim 4, wherein:

$R_3$ and $R_6$ are independently fluoro, chloro, phenyl, pyridyl, $C_1$-$C_3$ alkoxy, cyano or aryl halide.

6. The compound of claim 1, wherein X and Y are independently $C_1$-$C_{10}$ acyl or $C_1$-$C_{10}$ acyloxymethyl.

7. The compound of claim 1, wherein Z is alkoxyaryl.

8. The compound of claim 7, wherein the alkoxyaryl Z is 2'-alkoxyaryl.

9. The compound of claim 1, wherein the sum of m+n is 2.

10. The compound of claim 1, wherein the sum of m+n is 3.

11. The compound of claim 1, wherein the sum of m+n is 4.

12. The compound of claim 1, wherein the compound is of Formula 2:

Formula 2

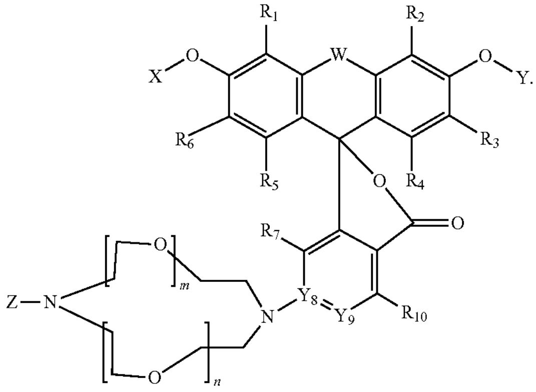

13. The compound of claim 12, wherein:

$R_1$-$R_7$, $R_9$ and $R_{10}$ are independently H, alkyl, chloro, fluoro, carboxy, substituted carboxy, alkoxy, aryloxy, aryl or heteroaryl;

m and n are independently 0, 1, 2 or 3, wherein the sum of m+n is 2, 3 or 4;

W is O, N—$R_{31}$, $C(R_{31}R_{32})$, $Si(R_{31}R_{32})$, S═O, O═S═O, P—$R_{32}$, O═P—$R_{32}$, O═P—$OR_{32}$, or $B(OR_{31})$, wherein $R_{31}$ and $R_{32}$ are independently selected from alkyl, aryl, or heteroaryl;

X and Y are independently $C_1$-$C_{10}$ acyl or $C_1$-$C_{10}$ acyloxymethyl; and Z is 2'-alkoxyaryl.

14. The compound of claim 12, wherein:

$R_1$-$R_7$, $R_9$ and $R_{10}$ are independently H, alkyl, chloro, fluoro, alkoxy, aryloxy, aryl or heteroaryl;

m and n are independently 1 or 2;

W is O, N—$R_{31}$, $C(R_{31}R_{32})$, $Si(R_{31}R_{32})$, O═P—$R_{32}$, O—P—$OR_{32}$, or $B(OR_{31})$, wherein $R_{31}$ and $R_{32}$ are independently selected from alkyl, aryl, or heteroaryl;

X and Y are independently acetyl or acetoxymethyl; and

Z is 2'-alkoxyaryl.

15. The compound of claim 12, wherein the compound is of Formula 2A

Formula 2A

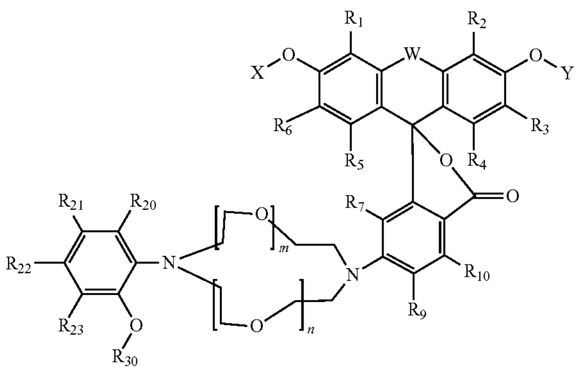

wherein:

$R_{20}$-$R_{23}$ are independently H, alkyl, substituted alkyl, halogen, carboxy, substituted carboxy, alkoxy, substituted alkoxy, azido, cyano, carbonyl, aryl, substituted aryl, heteroaryl or substituted heteroaryl;

$R_{30}$ is alkyl, substituted alkyl, aryl, substituted aryl, heteroaryl or substituted heteroaryl;

W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently selected from alkyl, aryl, or heteroaryl; and X and Y are independently acetyl or acetoxymethyl.

16. The compound of claim 15, wherein $R_{20}$-$R_{23}$ are independently H, alkyl, halogen, carboxy, substituted carboxy, alkoxy, aryloxy, alkylthiol, arylthiol, azido, cyano, carbonyl, aryl or heteroaryl; and $R_{30}$ is alkyl, aryl, or heteroaryl.

17. The compound of claim 15, wherein:

$R_1$-$R_7$, $R_9$, $R_{10}$, and $R_{20}$-$R_{23}$ are independently H, alkyl, halogen, carboxy, substituted carboxy, alkoxy, aryloxy, cyano, aryl or heteroaryl;

m and n are independently an integer from 0 to 3, wherein the sum of m+n is 2, 3 or 4;

W is O, N—$R_{31}$, C($R_{31}R_{32}$), Si($R_{31}R_{32}$), O—P—$R_{32}$, O—P—O$R_{32}$, or B(O$R_{31}$), wherein $R_{31}$ and $R_{32}$ are independently alkyl, aryl, or heteroaryl; and X and Y are independently acetyl or acetoxymethyl.

18. The compound of claim 15, wherein:

$R_1$-$R_7$, $R_9$, $R_{10}$, and $R_{20}$-$R_{23}$ are independently H, alkyl, chloro, fluoro, alkoxy, aryloxy, aryl or heteroaryl;

m and n are independently 1 or 2;

W is O, N—$R_{31}$, C($R_{31}R_{32}$), Si($R_{31}R_{32}$), O═P—$R_{32}$, or O═P—O$R_{32}$, wherein $R_{31}$ and $R_{32}$ are independently methyl, ethyl, propyl, butyl, benzyl, phenyl, or pyridyl; and X and Y are independently acetyl or acetoxymethyl.

19. The compound of claim 15, wherein at least one of $R_7$ and $R_9$ is alkoxy or aryloxy.

20. The compound of claim 1, wherein the compound is of Formula 3:

Formula 3

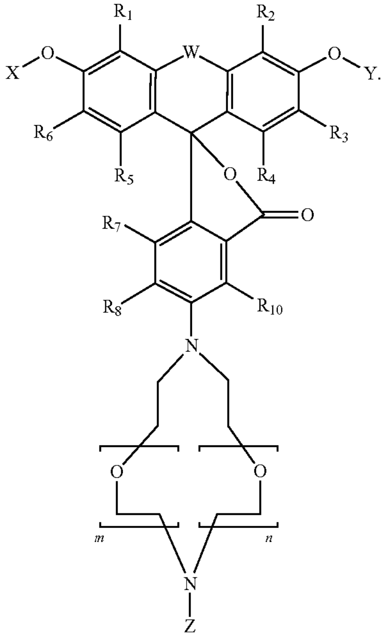

21. The compound of claim 20, wherein:

$R_1$-$R_{10}$ are independently H, chloro, fluoro, carboxy, substituted carboxy, cyano, alkoxy, aryloxy, aryl, heteroaryl, substituted alkoxy, substituted aryl, or substituted heteroaryl;

m and n are independently 0, 1, 2 or 3, wherein the sum of m+n is 2, 3 or 4;

W is O, N—$R_{31}$, C($R_{31}R_{32}$), Si($R_{31}R_{32}$), S═O, O═S—O, P—$R_{32}$, O═P—$R_{32}$, O═P—O$R_{32}$, or B(O$R_{31}$), wherein $R_{31}$ and $R_{32}$ are independently selected from H, alkyl, aryl, or heteroaryl;

X and Y are independently $C_1$-$C_{10}$ acyl or $C_1$-$C_{10}$ acyloxymethyl; and Z is 2'-alkoxyaryl.

22. The compound of claim 20, wherein:

$R_1$-$R_{10}$ are independently H, alkyl, chloro, fluoro, alkoxy, aryloxy, aryl or heteroaryl;

m and n are independently 1 or 2;

W is O, N—$R_{31}$, C($R_{31}R_{32}$), Si($R_{31}R_{32}$), O═P—$R_{32}$, or O═P—O$R_{32}$, wherein $R_{31}$ and $R_{32}$ are independently selected from alkyl, aryl, or heteroaryl;

X and Y are independently acetyl or acetoxymethyl; and

Z is 2'-alkoxyaryl.

23. The compound of claim 20, wherein the compound is of Formula 3A

Formula 3A

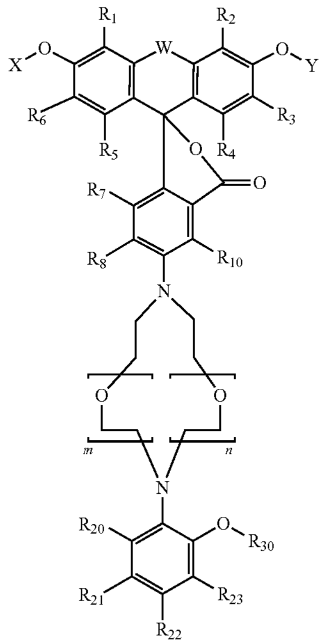

wherein:

$R_{20}$-$R_{23}$ are independently H, alkyl, substituted alkyl, halogen, carboxy, substituted carboxy, alkoxy, substituted alkoxy, azido, cyano, carbonyl, aryl, substituted aryl, heteroaryl, or substituted heteroaryl; and $R_{30}$ is alkyl, substituted alkyl, aryl, substituted aryl, heteroaryl or substituted heteroaryl;

W is O, N—$R_{31}$, C($R_{31}R_{32}$), Si($R_{31}R_{32}$), S═O, O═S═O, P—$R_{32}$, O═P—$R_{32}$, O═P—O$R_{32}$, or B(O$R_{31}$), wherein $R_{31}$ and $R_{32}$ are independently selected from alkyl, aryl, or heteroaryl; and X and Y are independently acetyl or acetoxymethyl.

24. The compound of claim 23, wherein $R_{20}$-$R_{23}$ are independently H, alkyl, halogen, carboxy, substituted carboxy, alkoxy, aryloxy, alkylthiol, arylthiol, azido, cyano, carbonyl, aryl or heteroaryl; and $R_{30}$ is alkyl, aryl, or heteroaryl.

25. The compound of claim 23, wherein:

$R_1$-$R_8$, $R_{10}$, and $R_{20}$-$R_{23}$ are independently H, alkyl, halogen, carboxy, substituted carboxy, alkoxy, aryloxy, cyano, aryl or heteroaryl;

m and n are independently an integer from 0 to 3, wherein the sum of m+n is 2, 3 or 4;

W is O, N—$R_{31}$, C($R_{31}R_{32}$), Si($R_{31}R_{32}$), O═P—$R_{32}$, O═P—O$R_{32}$, or B(O$R_{31}$), wherein $R_{31}$ and $R_{32}$ are independently alkyl, aryl, or heteroaryl; and X and Y are independently acetyl or acetoxymethyl.

26. The compound of claim 23, wherein:

$R_1$-$R_8$, $R_{10}$, and $R_{20}$-$R_{23}$ are independently H, alkyl, chloro, fluoro, alkoxy, aryloxy, aryl or heteroaryl;

m and n are independently 1 or 2;

W is O, N—$R_{31}$, C($R_{31}R_{32}$), Si($R_{31}R_{32}$), O═P—$R_{32}$, or O═P—O$R_{32}$, wherein $R_{31}$ and $R_{32}$ are independently methyl, ethyl, propyl, butyl, benzyl, phenyl, or pyridyl; and X and Y are each independently acetyl or acetoxymethyl.

27. The compound of claim 26, wherein at least one of Rs and $R_{10}$ is alkoxy or aryloxy.

28. A method of detecting, assessing and/or determining levels of intracellular lithium, sodium or potassium ion, the method comprising:

a) contacting a sample containing a cell with a compound according to claim 1;

b) incubating the sample under conditions in which the compound is loaded into the cell and an indicator compound comprising bound lithium, sodium or potassium ion is produced intracellularly;

c) illuminating the sample at a wavelength that generates a fluorescence response from the indicator compound, if present; and d) assessing the fluorescence response from the indicator compound.

29. The method of claim 28, further comprising one or more of:

stimulating the cell in the sample;

monitoring the fluorescence response from the indicator compound to assess a change in fluorescence intensity; and correlating a change in fluorescence intensity with a change in intracellular lithium, sodium or potassium ion level.

30. The method of claim 28, further comprising adding a cell-impermeant and non-fluorescent dye to the sample.

31. A kit for performing an intracellular lithium, sodium or potassium ion assay on a sample, the kit comprising:

one or more compounds according to claim 1; and one or more components selected from a buffer, an organic solvent, one or more detection reagents, luminescence standards, an enzyme, an enzyme indicator, non-fluorescent and cell-impermeant quencher dye, and an instruction sheet concerning the use of the kit for detecting a biological activity in a sample.

32. The compound of claim 1, wherein the compound is selected from:

| Compound | Chemical Structure |
|---|---|
| 17 | 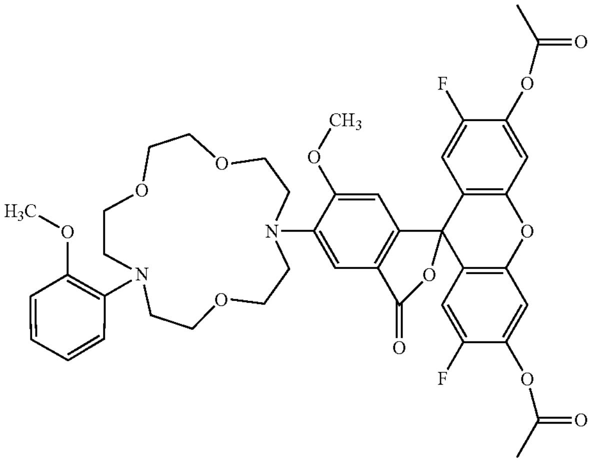 [SMILES: COc1ccccc1N1CCOCCOCCN(c2cc3c(cc2OC)C2(OC3=O)c3cc(F)c(OC(C)=O)cc3Oc3cc(OC(C)=O)c(F)cc32)CCOCC1] |
| 25 | 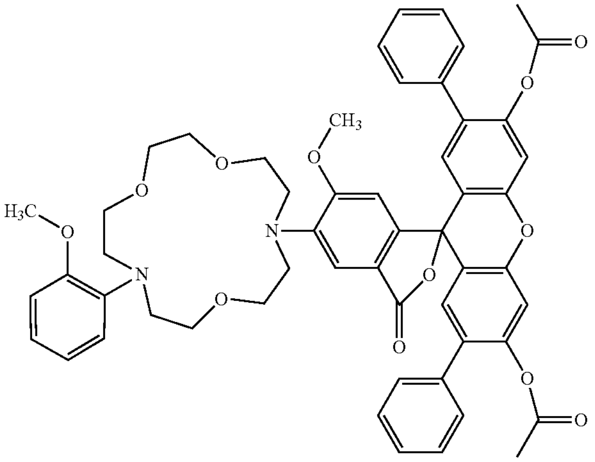 |
| 26 | 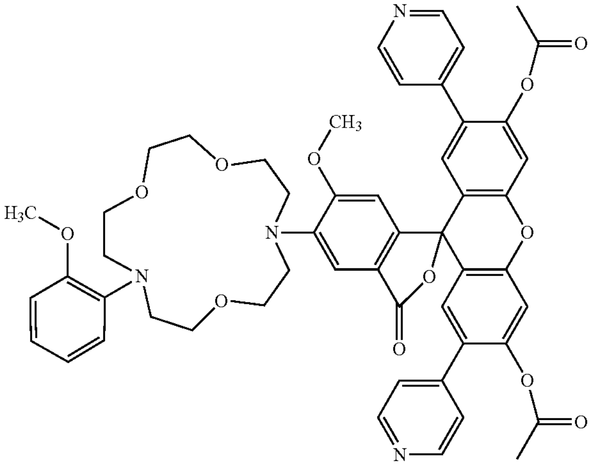 [SMILES: COc1ccccc1N1CCOCCOCCN(c2cc3c(cc2OC)C2(OC3=O)c3cc(-c4ccncc4)c(OC(C)=O)cc3Oc3cc(OC(C)=O)c(-c4ccncc4)cc32)CCOCC1] |

-continued
| Compound | Chemical Structure |
| --- | --- |
| 27 | 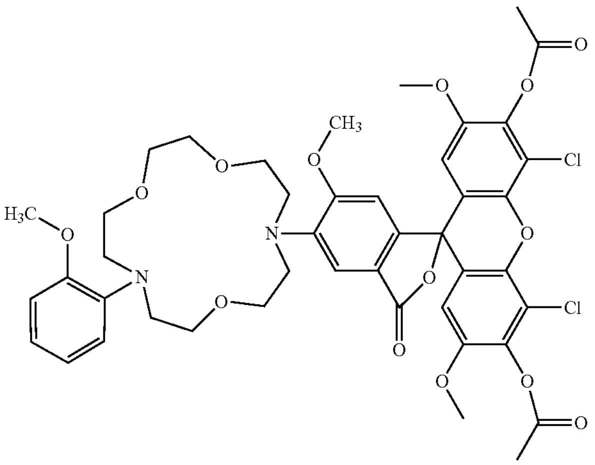 [SMILES: COc1ccccc1N1CCOCCOCCN(c2cc3c(cc2OC)C2(OC3=O)c3cc(OC)c(OC(C)=O)c(Cl)c3Oc3c2cc(OC)c(OC(C)=O)c3Cl)CCOCC1] |
| 28 | 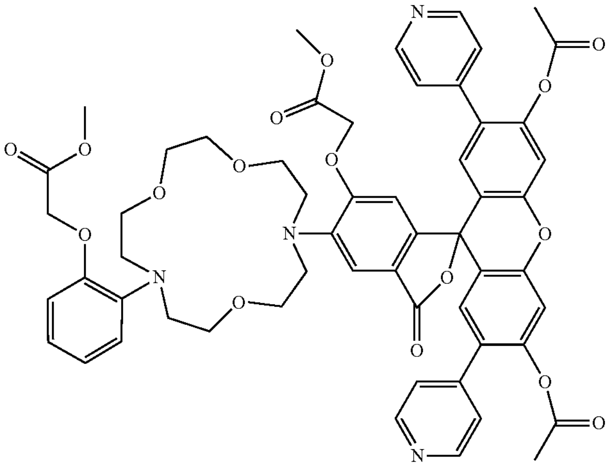 [SMILES: COC(=O)COc1ccccc1N1CCOCCOCCN(c2cc3c(cc2OCC(=O)OC)C2(OC3=O)c3cc(-c4ccncc4)c(OC(C)=O)cc3Oc3cc(OC(C)=O)c(-c4ccncc4)cc32)CCOCC1] |
| 29 | 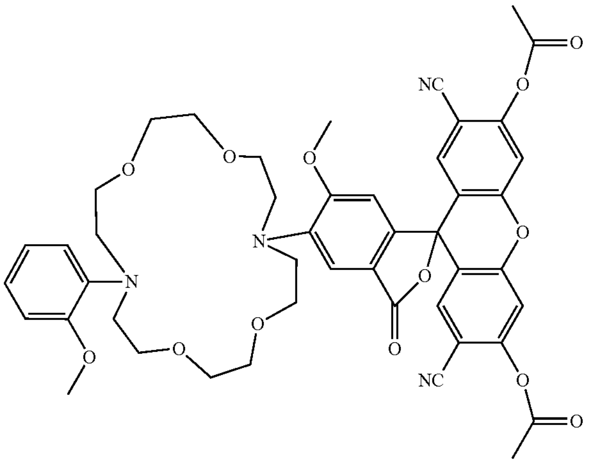 [SMILES: COc1ccccc1N1CCOCCOCCN(c2cc3c(cc2OC)C2(OC3=O)c3cc(C#N)c(OC(C)=O)cc3Oc3cc(OC(C)=O)c(C#N)cc32)CCOCCOCC1] |

-continued
| Compound | Chemical Structure |
|---|---|
| 30 | 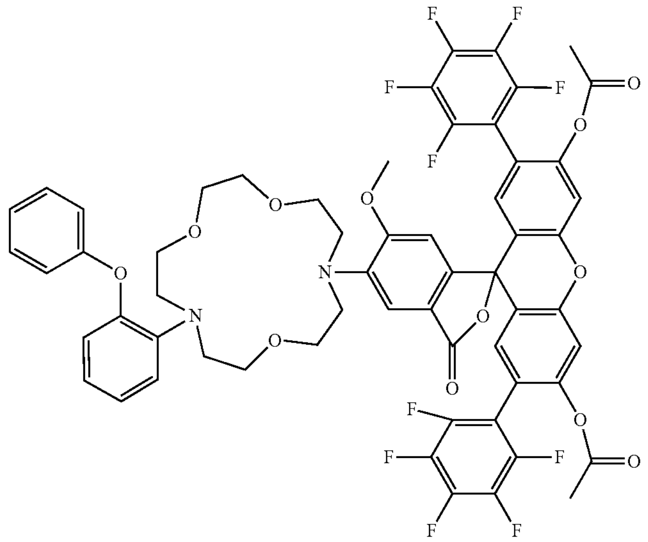 [SMILES: COc1cc2c(cc1N1CCOCCOCCN(c3ccccc3Oc3ccccc3)CCOCC1)C(=O)OC21c2cc(-c3c(F)c(F)c(F)c(F)c3F)c(OC(C)=O)cc2Oc2cc(OC(C)=O)c(-c3c(F)c(F)c(F)c(F)c3F)cc21] |
| 31 | 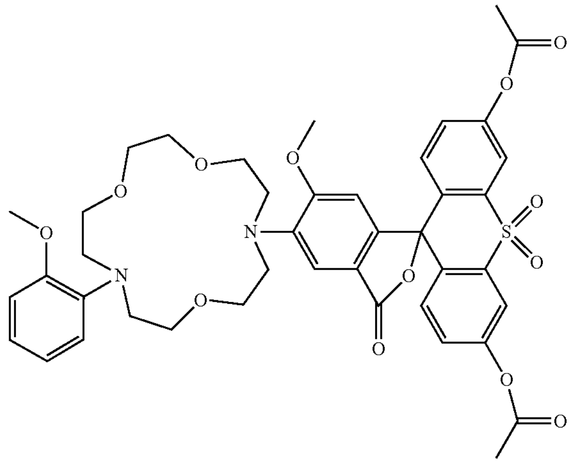 [SMILES: COc1ccccc1N1CCOCCOCCN(c2cc3c(cc2OC)C2(OC3=O)c3ccc(OC(C)=O)cc3S(=O)(=O)c3cc(OC(C)=O)ccc32)CCOCC1] |
| 32 | 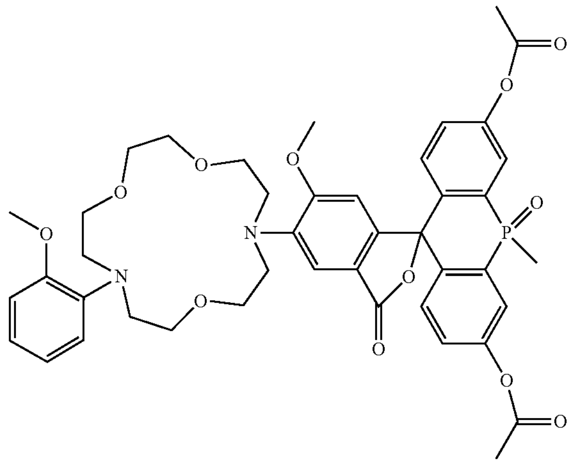 [SMILES: COc1ccccc1N1CCOCCOCCN(c2cc3c(cc2OC)C2(OC3=O)c3ccc(OC(C)=O)cc3P(C)(=O)c3cc(OC(C)=O)ccc32)CCOCC1] |

-continued
| Compound | Chemical Structure |
|---|---|
| 33 | 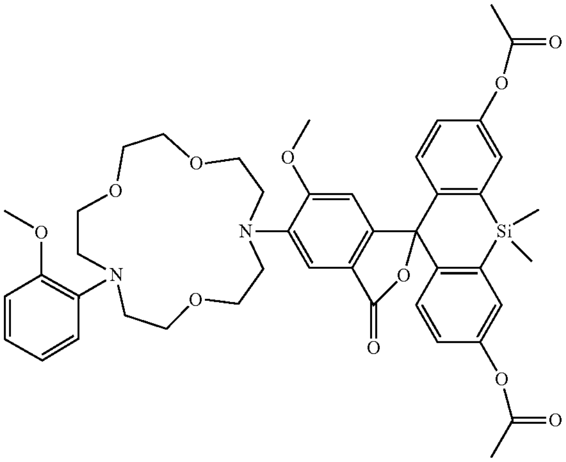 [SMILES: COc1ccccc1N1CCOCCOCCN(c2cc3c(cc2OC)C2(OC3=O)c3ccc(OC(C)=O)cc3[Si](C)(C)c3cc(OC(C)=O)ccc32)CCOCC1] |
| 34 | 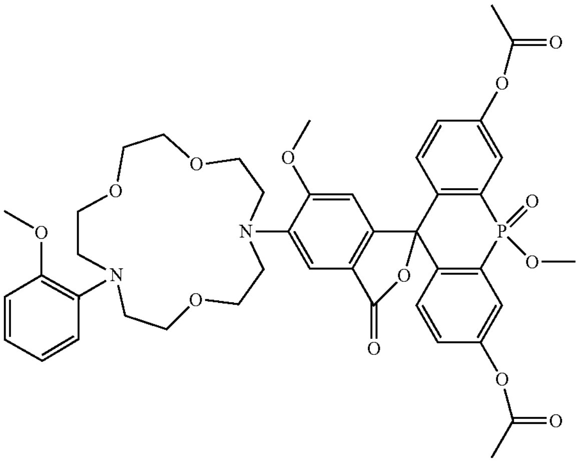 |
| 35 | 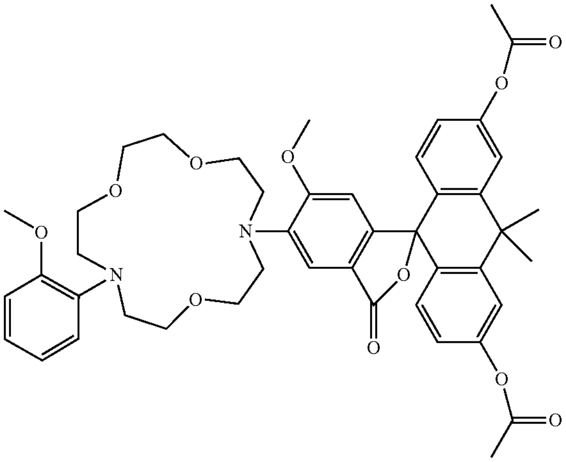 [SMILES: COc1ccccc1N1CCOCCOCCN(c2cc3c(cc2OC)C2(OC3=O)c3ccc(OC(C)=O)cc3C(C)(C)c3cc(OC(C)=O)ccc32)CCOCC1] |

-continued
| Compound | Chemical Structure |
|---|---|
| 36 | 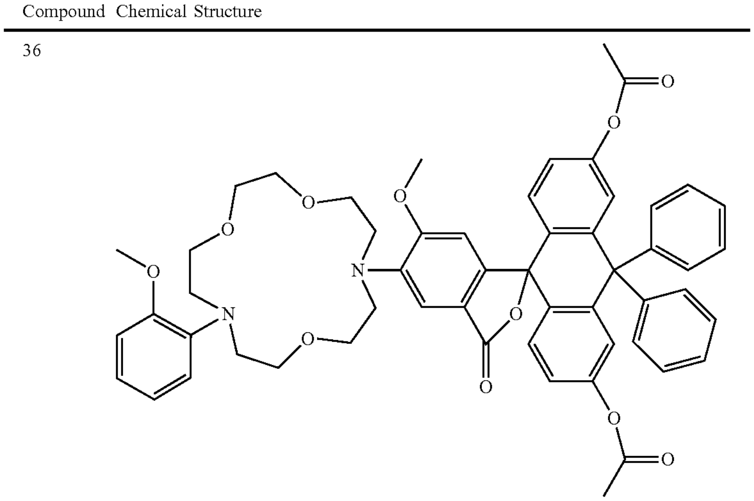 |
* * * * *